United States Patent
Chen et al.

(10) Patent No.: US 10,047,166 B2
(45) Date of Patent: Aug. 14, 2018

(54) HUMANIZED ANTI-IGE ANTIBODIES THAT CROSSLINK CD23 ON B LYMPHOCYTES BUT DO NOT SENSITIZE MAST CELLS

(71) Applicant: Academia Sinica, Taipei (TW)

(72) Inventors: Jiun-Bo Chen, Taipei (TW); Yu-Yu Shiung, Taipei (TW); Tse-Wen Chang, Taipei (TW)

(*) Notice: Subject to any disclaimer, the term of this patent is extended or adjusted under 35 U.S.C. 154(b) by 0 days.

(21) Appl. No.: 15/318,360

(22) PCT Filed: Jun. 16, 2015

(86) PCT No.: PCT/US2015/035981
§ 371 (c)(1),
(2) Date: Dec. 13, 2016

(87) PCT Pub. No.: WO2015/195631
PCT Pub. Date: Dec. 23, 2015

(65) Prior Publication Data
US 2017/0121425 A1    May 4, 2017

Related U.S. Application Data

(60) Provisional application No. 62/013,196, filed on Jun. 17, 2014.

(51) Int. Cl.
*A61K 39/395* (2006.01)
*C07K 16/42* (2006.01)
*C07K 16/28* (2006.01)

(52) U.S. Cl.
CPC ...... *C07K 16/4291* (2013.01); *C07K 16/2851* (2013.01); *C07K 2317/24* (2013.01); *C07K 2317/33* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 5,530,101 A * | 6/1996 | Queen | C07K 16/00 | 424/133.1 |
| 5,585,089 A * | 12/1996 | Queen | C07K 16/00 | 424/133.1 |
| 5,693,761 A * | 12/1997 | Queen | C07K 16/00 | 435/252.3 |
| 5,693,762 A * | 12/1997 | Queen | C07K 16/00 | 424/133.1 |
| 5,958,708 A * | 9/1999 | Hardman | C07K 16/4291 | 435/7.21 |
| 5,994,511 A * | 11/1999 | Lowman | C07K 16/00 | 530/387.3 |
| 6,037,453 A * | 3/2000 | Jardieu | C07K 16/4291 | 530/387.3 |
| 6,066,718 A * | 5/2000 | Hardman | C07K 16/4291 | 435/326 |
| 6,180,370 B1 * | 1/2001 | Queen | C07K 16/00 | 424/133.1 |
| 6,685,939 B2 * | 2/2004 | Jardieu | C07K 16/00 | 424/130.1 |
| 6,914,129 B2 * | 7/2005 | Jardieu | C07K 16/00 | 424/133.1 |
| 7,022,500 B1 * | 4/2006 | Queen | C07K 16/00 | 424/130.1 |
| 7,253,263 B1 * | 8/2007 | Hanai | C07K 16/18 | 424/133.1 |
| 7,531,169 B2 * | 5/2009 | Singh | C07K 16/005 | 424/130.1 |
| 8,071,097 B2 * | 12/2011 | Wu | A01K 67/0278 | 424/133.1 |
| 8,080,249 B2 * | 12/2011 | Risk | C07K 16/4291 | 424/133.1 |
| 9,587,034 B2 * | 3/2017 | Chang | C07K 16/4291 | |
| 2002/0076404 A1 * | 6/2002 | Chang | C07K 16/4291 | 424/131.1 |
| 2004/0171816 A1 * | 9/2004 | Schenk | A61K 47/646 | 530/388.15 |
| 2005/0214857 A1 * | 9/2005 | Lasters | C07K 16/00 | 435/7.1 |
| 2005/0288491 A1 * | 12/2005 | Wilson | C07K 16/1027 | 530/388.15 |
| 2006/0134098 A1 * | 6/2006 | Bebbington | C07K 16/005 | 424/130.1 |
| 2011/0312505 A1 * | 12/2011 | Reddy | C07K 16/065 | 506/2 |

OTHER PUBLICATIONS

Janeway et al., Immunobiology, 3rd edition, 1997, Garland Publishing, Inc., pp. 3:1-3:11.*
Rudikoff et al., Proc Natl Acad Sci U S A. Mar. 1982;79(6):1979-83.*
Shiung et al., Immunobiology. Jul. 2012;217(7):676-83. doi: 10.1016/j.imbio.2011.11.006. Epub Nov. 25, 2011.*
Kipriyanov et al., Mol Biotechnol. Jan. 2004;26(1):39-60.*

* cited by examiner

*Primary Examiner* — Michael Szperka

(57) ABSTRACT

A novel humanized anti-IgE antibody is disclosed. The antibody is capable of binding to free IgE, membrane-bound IgE on B lymphocytes, IgE bound by CD23, but not to IgE bound by high-affinity IgE.Fc receptor on mast cells. The present invention relates to the treatment of IgE-mediated diseases, including allergic asthma, allergic rhinitis, atopic dermatitis, food allergy, chronic spontaneous (idiopathic) urticaria, chronic rhinosinusitis, systemic mastocytosis, cutaneous mastocytosis, allergic bronchopulmonary aspergillosis, recurrent idiopathic angioedema, and eosinophil-associated gastrointestinal disorder by administering the anti-IgE antibody of the present invention.

13 Claims, 18 Drawing Sheets

```
       1               10        20        30        40        50
VH1-69/JH4   QVQLVQSGAEVKKPGSSVKVSCKASGGTFSSYAISWVRQAPGQGLEWMGG
mu8D6 VH     QVQLQQSGAELAKPGASVMLSCKASGYTFNGYWMHWVKQRPGQDLEWIGY
hu8D6 VH     QVQLVQSGAEVKKPGSSVKVSCKASGYTFNGYWMHWVRQAPGQGLEWIGY
                                                              *

51a          60        70        80 abc           90
VH1-69/JH4   IIPIFGTANYAQKFQGRVTITADESTSTAYMELSSLRSEDTAVYYCAR--
mu8D6 VH     INPTTGHTEYNQKFKDKATLTADESSNTAYIELSSLTSDDSAVYYCARQE
hu8D6 VH     INPTTGHTEYNQKFKDKATITADESTNTAYMELSSLRSEDTAVYYCARQE
                                *                     **

100       110
VH1-69/JH4   ----YFDYWGQGTLVTVSS (SEQ ID NO: 11)
mu8D6 VH     YRHSWFAYWGQGTLVTVSA (SEQ ID NO: 1)
hu8D6 VH     YRHSWFAYWGQGTLVTVSS (SEQ ID NO: 2)
```

FIG. 1

```
                1               10              20         abcd  30              40
Vκ1-39/Jκ1      DIQMTQSPSSLSASVGDRVTITCRASQSIS----SYLNWYQQKPGKAPKL
mu8D6 Vκ        DIVLTQSPASLAVSLGQRATISCKASQSVDYDGDTYMNWYHQKPGQPPKL
hu8D6 Vκ        DIQLTQSPSSLSASVGDRVTITCRASQSVDYDGDTYMNWYQQKPGKAPKL
                  *
                50              60              70              80              90
Vκ1-39/Jκ1      LIYAASSLQSGVPSRFSGSGSGTDFTLTISSLQPEDFATYYCQQS-YSTW
mu8D6 Vκ        LIYAASNLDSGIPARFSGSGSGTDFTLNIHPVEEEDAATYYCQQTNEDPW
hu8D6 Vκ        LIYAASNLDSGVPSRFSGSGSGTDFTLTISSLQPEDFATYYCQQTNEDPW 100  107
Vκ1-39/Jκ1      TFGQGTKVEIKR  (SEQ ID NO:12)
mu8D6 Vκ        TFGGGTKLEIKR  (SEQ ID NO: 3)
hu8D6 Vκ        TFGQGTKVEIKR  (SEQ ID NO: 4)
```

FIG. 2

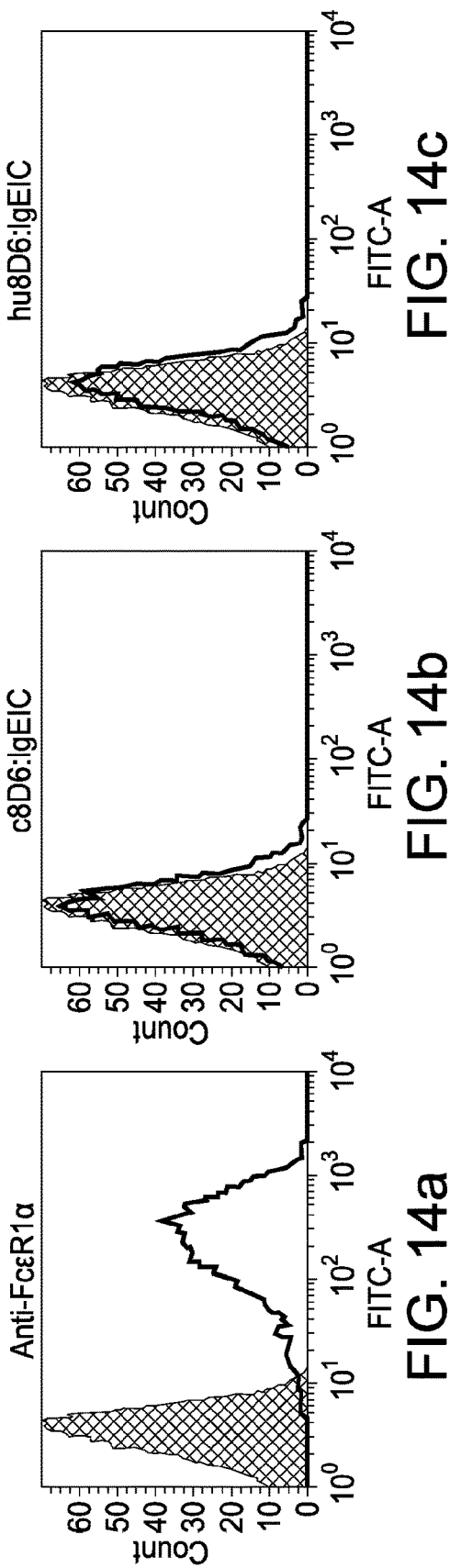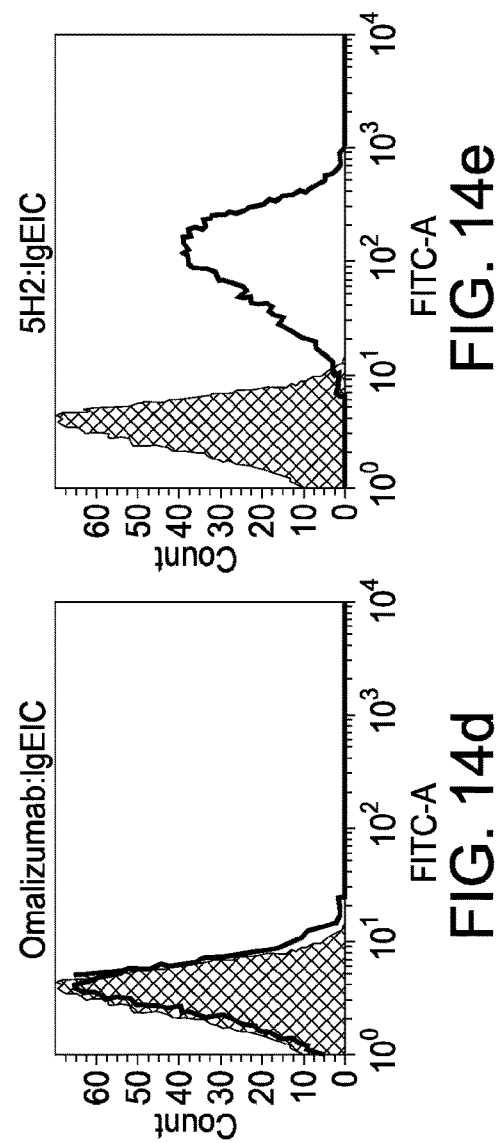

SEQUENCE LISTING

<160> NUMBER OF SEQ ID NOS: 12

<210> SEQ ID NO 1
<211> LENGTH: 119
<212> TYPE: PRT
<213> ORGANISM: Mus sp.
<220> FEATURE:
<223> OTHER INFORMATION: variable region of heavy chain derived from 8D6 hybridoma

<400> SEQUENCE: 1

```
Gln Val Gln Leu Gln Gln Ser Gly Ala Glu Leu Ala Lys Pro Gly Ala
1               5                   10                  15

Ser Val Met Leu Ser Cys Lys Ala Ser Gly Tyr Thr Phe Asn Gly Tyr
            20                  25                  30

Trp Met His Trp Val Lys Gln Arg Pro Gly Gln Asp Leu Glu Trp Ile
        35                  40                  45

Gly Tyr Ile Asn Pro Thr Thr Gly His Thr Glu Tyr Asn Gln Lys Phe
    50                  55                  60

Lys Asp Lys Ala Thr Leu Thr Ala Asp Glu Ser Ser Asn Thr Ala Tyr
65                  70                  75                  80

Ile Glu Leu Ser Ser Leu Thr Ser Asp Asp Ser Ala Val Tyr Tyr Cys
                85                  90                  95

Ala Arg Gln Glu Tyr Arg His Ser Trp Phe Ala Tyr Trp Gly Gln Gly
            100                 105                 110

Thr Leu Val Thr Val Ser Ala
        115
```

<210> SEQ ID NO 2
<211> LENGTH: 119
<212> TYPE: PRT
<213> ORGANISM: Artificial Sequence
<220> FEATURE:
<223> OTHER INFORMATION: humanized variable region of heavy chain

<400> SEQUENCE: 2

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Asn Gly Tyr
            20                  25                  30

Trp Met His Trp Val Arg Gln Ala Pro Gly Gln Gly Leu Glu Trp Ile
```

```
                35                  40                  45
Gly Tyr Ile Asn Pro Thr Thr Gly His Thr Glu Tyr Asn Gln Lys Phe
     50                  55                  60

Lys Asp Lys Ala Thr Ile Thr Ala Asp Glu Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gln Glu Tyr Arg His Ser Trp Phe Ala Tyr Trp Gly Gln Gly
                100                 105                 110

Thr Leu Val Thr Val Ser Ser
            115

<210> SEQ ID NO 3
<211> LENGTH: 111
<212> TYPE: PRT
<213> ORGANISM: Mus sp.
<220> FEATURE:
<223> OTHER INFORMATION: variable region of light chain derived from 8D6
      hybridoma

<400> SEQUENCE: 3

Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
                 20                  25                  30

Gly Asp Thr Tyr Met Asn Trp Tyr His Gln Lys Pro Gly Gln Pro Pro
             35                  40                  45

Lys Leu Leu Ile Tyr Ala Ala Ser Asn Leu Asp Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Thr Asn
                 85                  90                  95

Glu Asp Pro Trp Thr Phe Gly Gly Gly Thr Lys Leu Glu Ile Lys
                100                 105                 110

<210> SEQ ID NO 4
<211> LENGTH: 111
<212> TYPE: PRT
<213> ORGANISM: Artificial Sequence
<220> FEATURE:
<223> OTHER INFORMATION: humanized variable region of light chain

<400> SEQUENCE: 4

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Ser Val Asp Tyr Asp
                 20                  25                  30

Gly Asp Thr Tyr Met Asn Trp Tyr Gln Gln Lys Pro Gly Lys Ala Pro
             35                  40                  45

Lys Leu Leu Ile Tyr Ala Ala Ser Asn Leu Asp Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Thr Asn
                 85                  90                  95

Glu Asp Pro Trp Thr Phe Gly Gln Gly Thr Lys Val Glu Ile Lys
                100                 105                 110
```

```
<210> SEQ ID NO 5
<211> LENGTH: 10
<212> TYPE: PRT
<213> ORGANISM: Mus sp.
<220> FEATURE:
<223> OTHER INFORMATION: complementarity determining region 1 derived
      from the heavy chain of mu8D6 antibody

<400> SEQUENCE: 5

Gly Tyr Thr Phe Asn Gly Tyr Trp Met His
1               5                   10

<210> SEQ ID NO 6
<211> LENGTH: 17
<212> TYPE: PRT
<213> ORGANISM: Mus sp.
<220> FEATURE:
<223> OTHER INFORMATION: complementarity determining region 2 derived
      from the heavy chain of mu8D6 antibody

<400> SEQUENCE: 6

Tyr Ile Asn Pro Thr Thr Gly His Thr Glu Tyr Asn Gln Lys Phe Lys
1               5                   10                  15

Asp

<210> SEQ ID NO 7
<211> LENGTH: 12
<212> TYPE: PRT
<213> ORGANISM: Mus sp.
<220> FEATURE:
<223> OTHER INFORMATION: complementarity determining region 3 derived
      from the heavy chain of mu8D6 antibody

<400> SEQUENCE: 7

Ala Arg Gln Glu Tyr Arg His Ser Trp Phe Ala Tyr
1               5                   10

<210> SEQ ID NO 8
<211> LENGTH: 10
<212> TYPE: PRT
<213> ORGANISM: Mus sp.
<220> FEATURE:
<223> OTHER INFORMATION: complementarity determining region 1 derived
      from the light chain of mu8D6 antibody

<400> SEQUENCE: 8

Gln Ser Val Asp Tyr Asp Gly Asp Thr Tyr
1               5                   10

<210> SEQ ID NO 9
<211> LENGTH: 7
<212> TYPE: PRT
<213> ORGANISM: Mus sp.
<220> FEATURE:
<223> OTHER INFORMATION: complementarity determining region 2 derived
      from the light chain of mu8D6 antibody

<400> SEQUENCE: 9

Ala Ala Ser Asn Leu Asp Ser
1               5

<210> SEQ ID NO 10
<211> LENGTH: 9
<212> TYPE: PRT
<213> ORGANISM: Mus sp.
<220> FEATURE:
```

<223> OTHER INFORMATION: complementarity determining region 3 derived
      from the light chain of mu8D6 antibody

<400> SEQUENCE: 10

Gln Gln Thr Asn Glu Asp Pro Trp Thr
1               5

<210> SEQ ID NO 11
<211> LENGTH: 113
<212> TYPE: PRT
<213> ORGANISM: Homo sapiens
<220> FEATURE:
<223> OTHER INFORMATION: the germline VH1-69/JH4 sequence of human
      immunoglobulin gene

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 12
<211> LENGTH: 107
<212> TYPE: PRT
<213> ORGANISM: Homo sapiens
<220> FEATURE:
<223> OTHER INFORMATION: the germline Vk1-39/Jk1 sequence of human
      immunoglobulin gene

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Trp Thr
                85                  90                  95

Phe Gly Gln Gly Thr Lys Val Glu Ile Lys Arg
            100                 105

HUMANIZED ANTI-IGE ANTIBODIES THAT CROSSLINK CD23 ON B LYMPHOCYTES BUT DO NOT SENSITIZE MAST CELLS

CROSS-REFERENCE TO RELATED APPLICATION

This application claims priority to U.S. provisional application No. 62/013,196, filed Jun. 17, 2014, the entireties of which is incorporated herein by reference.

BACKGROUND OF THE INVENTION

1. Field of the Invention

The present invention pertains to the preparation of humanized antibodies, which are capable of binding to free IgE, membrane-bound IgE on B lymphocytes, IgE bound by CD23, but not to IgE bound by high-affinity IgE.Fc receptors on mast cells. The invention also pertains to the therapeutic applications of such antibodies in treating IgE-mediated diseases, including allergic asthma, allergic rhinitis, atopic dermatitis, food allergy, chronic spontaneous (idiopathic) urticaria, chronic rhinosinusitis, systemic mastocytosis, cutaneous mastocytosis, allergic bronchopulmonary aspergillosis, recurrent idiopathic angioedema, and eosinophil-associated gastrointestinal disorder.

2. Description of Related Art

Allergy is a hypersensitive state induced by an exaggerated immune response to a foreign, harmless antigen. An immediate hypersensitivity response occurs through the interaction of immunoglobulin E (IgE) and the high-affinity IgE.Fc receptor (FcεRI) present on the surface of mast cells and basophils in the presence of allergen which is capable of reacting with the FcεRI-bound IgE, causing the release of performed and newly-synthesized mediators from these inflammatory cells. Most allergic diseases are IgE-mediated. It is well known that a number of non-allergic diseases, which do not involve an immune response to a foreign antigen, particularly inflammatory skin diseases, are also IgE-mediated.

There are two major receptor for IgE, FcεRI and the low-affinity IgE.Fc receptor FcεRII (also referred to as CD23). FcεRI is predominantly expressed on the surface of mast cells and basophils in humans, where it is a tetrameric complex consisting of one α-chain, one β-chain, and two disulfide-bound γ-chains. Activation of FcεRI on mast cells and basophils by allergens leads to degranulation, while activation of FcεRI on dendritic cells leads to IgE-mediated allergen presentation.

CD23 is a type II transmembrane glycoprotein of approximately 45 kDa molecular weight comprising a C-type lectin-like domain, followed by a stalk region, which bears several repeats that serve as a putative leucine zipper to form coiled-coil trimers, a single membrane-spanning region, and a short N-terminal cytoplasmic domain. Indeed, the affinity of monomeric CD23 to IgE (KD=$10^{-6}$-$10^{-7}$ M) is much lower than that of FcεRI (KD=about $10^{-10}$ M), but substantially increased in its trimeric form (KD=$10^{-8}$-$10^{-9}$ M). The FCER2 gene encoding CD23 polypeptide possesses 2 alternative transcription start sites driving synthesis of two mRNA variants which leads to produce two CD23 isoforms differing in the first seven (CD23a) and six (CD23b) amino acids of the N-terminal cytoplasmic tail. CD23a is exclusively and contiguously expressed by B cells, whereas CD23b is induced by IL-4 on the surface of monocyte/macrophage, B cells, T cells, eosinophils, dendritic cells, and epithelial cells. CD23 on B cells is thought to contribute to regulation of IgE production and antigen presentation, while CD23 on macrophages and dendritic cell is involved in phagocytosis/endocytosis, clearance of antigen-IgE complex and antigen presentation. Additional function of CD23 on epithelial cells includes the transportation of IgE. The antigen-IgE complex directly penetrate across the epithelium to the lumen space and vice versa. CD23 can also be released from cell surfaces as a range of free soluble CD23 (sCD23) proteins of 37, 33, 25, and 16 kDa. The predominant metalloprotease responsible for CD23 shedding in vivo is ADAM10 gene, which generates 37 kDa or 35 kDa sCD23 species in a trimeric form. A further naturally occurring sCD23 is derCD23 produced by action of the Der p1 protease found in the faeces of the house dust mite, *dermatophagoides pteronyssinus*. The cleavage of CD23 by Der p1 yields the 16 kDa monomeric derCD23. It is shown that trimeric sCD23 fragments were observed to be key molecules for potentiating spontaneous IgE synthesis, whereas the smaller monomeric sCD23 appears to down-regulate IL-4 stimulated IgE synthesis.

IgE exists in a secreted form and a membrane-bound form, which appears to be splicing variants. The constant regions of the ε chain of secreted form of IgE harbors $C_{H1}$-$C_{H2}$-$C_{H3}$-$C_{H4}$ domains, whereas the ε chain of membrane-bound form of IgE having a membrane-bound IgE (mIgE) is found in two isoforms as a result of alternative splicing in humans. The ε chain of both isoforms of human mIgE contains a migis-ε and a membrane-anchoring peptide. One isoform contains only the migis-ε peptide (15 amino acid long) between the CH4 domain and the membrane-anchoring peptide (referred to as "short form"), whereas the second isoform additionally contains an extra 52 amino acid long domain (referred to as CεmX domain) between the $C_{H4}$ domain and the migis-ε peptide (referred to as "long form").

Since IgE plays a central role in mediating most allergic diseases, several strategies have been proposed to control IgE levels in the body or to regulate IgE synthesis, such as anti-IgE, anti-IL-4/IL-13 and anti-CD23. Omalizumab (Xolair®) is a recombinant humanized monoclonal anti-IgE antibody that binds to free IgE circulating in the serum and membrane-bound IgE on B cells but not FcεRI-bound and CD23-bound IgE on cell surface. Omalizumab causes significant (up to 99%) reduction of serum free IgE in allergic patients, leading to inhibit IgE binding to FcεRI and subsequently a down-regulation of FcεRI on basophils and mast cells. Numerous clinical trials in many IgE-mediated diseases, such as allergic asthma, chronic urticaria, allergic rhinitis, atopic dermatitis, etc., have shown that Omalizumab is efficacious and safe in treating these diseases. Omalizumab has been approved for treating severe allergic asthma and chronic idiopathic urticaria in many countries. Moreover, lumiliximab, which is an anti-CD23 monoclonal antibody consisting of primate (cynomolgus macaque) variable regions and human constant regions, is found to bind to the C-type lectin domain preventing IgE from binding to CD23, thus leading to stabilization of surface CD23 and reduction of the proteolytic cleavage of CD23. Lumiliximab has been reported to inhibit the germline ε transcripts, decrease the IgE production of human peripheral blood mononuclear cell (PBMCs) in culture, and reduce blood IgE levels in allergic patients.

In a 1990 patent (U.S. Pat. No. 4,940,782), a murine IgG monoclonal antibody 44.7b specific for rat IgE, which is capable of binding to CD23-bound IgE but not IgE bound to FcεRI, was disclosed. This antibody 44.7b was never pursued as a therapeutic candidate for treating IgE-mediated diseases. A paper published in 2012 (Shiung et al., *Immunobiology*, 2012, 217:676-683) reported the discovery of a murine anti-human IgE monoclonal antibody, 8D6, which is capable of binding to CD23-bound IgE but not IgE bound to FcεRI. The authors suggested that this antibody possesses not only the major pharmacologic properties of Omalizumab to neutralize IgE without sensitizing mast cells and basophils but also the property of lumiliximab through cross-linking IgE bound to CD23. However, the murine antibody may be immunogenic and cannot be applied for treating IgE-mediated diseases. The murine antibody for therapeutic applications in man has been found to be limited by immune responses made by patients to the murine antibodies. Thus, the humanization of murine antibodies is necessary to reduce immunogenicity in human recipients.

SUMMARY

The present invention pertains to humanized antibodies that bind to (1) human IgE in its secreted free form, (2) to membrane-bound IgE on B lymphocytes, and (3) to IgE bound by CD23 on B cells and by free CD23 in solution. Such anti-IgE antibodies do not bind to IgE bound by FcεRI on mast cells and basophils and hence do not activate those inflammatory cells. The present invention also pertains to the biological properties of those humanized anti-IgE antibodies in the biosynthesis of IgE, the binding of IgE to various cellular and molecular components, and the potential clearing effects of allergens. It also pertains to the application of such antibodies in the treatment of IgE-mediated allergic and non-allergic diseases.

We have recognized that the latest results of the phase Ib and IIa trials of the anti-M1' antibody, MEMP1972A (Gauvreau et al., *Science Translation Medicine*, 2014, Vol. 6: 243ra85), suggested that by inhibiting new IgE synthesis, IgE-mediated symptoms can be decreased. We also conceptualize that since hu8D6:IgE complexes can bind to CD23 and since CD23 is expressed in numerous cell types (Acharya et al. Clin. Exp. Immunol., 2010, 162:12-23), the absorption of hu8D6:IgE complexes to cell surface CD23 can reduce the total IgE levels (free and hu8D6-bound IgE) in circulation in vivo. Besides, epithelial cells along the mucosal lining are capable of clearing cell-bound substances through CD23-dependent transcytosis (Tu et al. Gastroenterology, 2005, 129:928-940), hu8D6 may facilitate the mopping up and removal of incoming allergens and endogenous IgE-binding autoantigens when hu8D6:IgE complexes are transported into the lumen space of gastrointestinal and bronchoalveolar tracts. We also rationalize that the binding of hu8D6 to CD23-bound IgE can effectively cross-link CD23 on B lymphocytes to result in inhibition of antigen-specific IgE production by B cells upon activation by a specific antigen. Those properties of hu8D6 should support the potential utility that hu8D6 and other humanized antibodies with the same set of IgE-binding specificities can inhibit antigen-specific IgE production in patients with IgE-mediated diseases and hence ameliorate those diseases. Using murine 8D6 antibody as an example, we have prepared a humanized form of the antibody. This humanized antibody possesses all binding and biological properties discussed above.

REFERENCES (1) Bonita J. Rup, Larry E. Kahn, "Monoclonal antibodies against IgE-associated determinants, hybrid cell lines producing these antibodies, and use therefore" U.S. Pat. No. 4,940,782 (1990).

(2) Yu-Yu Shiung, Chen-Yi Chiang, Jiun-Bo Chen, Pheidias C. Wu, Alfur Fu-Hsin Hung, Donic Chien-Sheng Lu, Rong-Long Pan, Tse Wen Chang. "An anti-IgE monoclonal antibody that binds to IgE on CD23 but not on high-affinity IgE.Fc receptors, FcRn", *Immunobiology*., 217:676-683-9 (2012)

(3) Gail M. Gauvreau, Jeffrey M. Harris, Louis-Philippe Boulet, Heleen Scheerens, J. Mark Fitzgerald, Wendy S. Putnam, Donald W. Cockcroft, Beth E. Davis, Richard Leigh, Yanan Zheng, Barbro Dahlen, Yehong Wang, Romeo Maciuca, Irvin Mayers, X. Charlene Liao, Lawren C. Wu, John G. Matthews, Paul M. O'Byrne1, "Targeting membrane-expressed IgE B cell receptor with an antibody to the M1 prime epitope reduces IgE production", *Science Translation Medicine*., Vol. 6: 243ra85 (2014)

(4) M Acharya, G Borland, A L Edkins, L M MacLellan, J Matheson, B W Ozanne, and W Cushley, "CD23/FcεRII: molecular multi-tasking", *Clin. Exp. Immunol.*, 162(1): 12-23 (2010)

(5) Yahong Tu, Saad Salim, Jackie Bourgeois, Vincenza Di Leo, E. Jan Irvine, John K. Marshall, Mary H. Perdue, "CD23-Mediated IgE Transport Across Human Intestinal Epithelium: Inhibition by Blocking Sites of Translation or Binding", *Gastroenterology*, 129(3): p928-940(2005)

(6) Jiun-Bo Chen, Pheidias C. Wu, Alfur Fu-Hsin Hung, Chia-Yu Chu, Tsen-Fang Tsai, Hui-Ming Yu, Hwan-You Chang, and Tse Wen Chang, "Unique epitopes on CEmX in IgEB cell receptors are potentially applicable for targeting IgE-committed B cells", *J. Immunol.*, 184: 1748-1756 (2010)

(7) Wiegand T W, Williams P B, Dreskin S C, Jouvin M H, Kinet J P, Tasset D., "High-affinity oligonucleotide ligands to human IgE inhibit binding to Fc epsilon receptor I", *J. Immunol.*, 157: p221-230 (1996)

(8) Pathan N I, Chu P, Hariharan K, Cheney C, Molina A, Byrd J., "Mediation of apoptosis by and antitumor activity of lumiliximab in chronic lymphocytic leukemia cells and CD23+ lymphoma cell lines", *Blood*, 111(3):p1594-1602 (2008)

(9) Wan T, Beavil R L, Fabiane S M, Beavil A J, Sohi M K, Keown M, Young R J, Henry A J, Owens R J, Gould H J, Sutton R E, "The crystal structure of IgE Fc reveals an asymmetrically bent conformation", *Nature Immunol.*, 3(7):681-6 (2002)

BRIEF DESCRIPTION OF THE DRAWINGS

The present description will be better understood from the following detailed description read in light of the accompanying drawings, where:

FIG. 1 illustrates the alignment of amino acid sequences of variable heavy chains including human germline $V_H$1-69 and JH4 sequences ($V_H$1-69/JH4), murine anti-IgE antibody 8D6 (mu8D6), and 8D6-grafted humanized 8D6 (hu8D6). Complementarity determining regions (CDRs) are underlined. The amino acids of murine $V_H$ framework retained in hu8D6 are labeled by star.

FIG. 2 illustrates the alignment of amino acid sequences of variable light chains including human germline Vκ1-39 and Jκ1 sequences (Vκ1-39/Jκ1), murine anti-IgE antibody 8D6 (mu8D6), and 8D6-grafted humanized 8D6 (hu8D6). Complementarity determining regions (CDRs) are underlined. The amino acids of murine Vκ framework retained in hu8D6 are labeled by star.

FIGS. 14a to 14e illustrate the inability of the hu8D6:IgE immune complexes to bind to human FcɛRI-expressing RBL SX-38 cells.

DETAILED DESCRIPTION OF THE INVENTION

Figure 3:
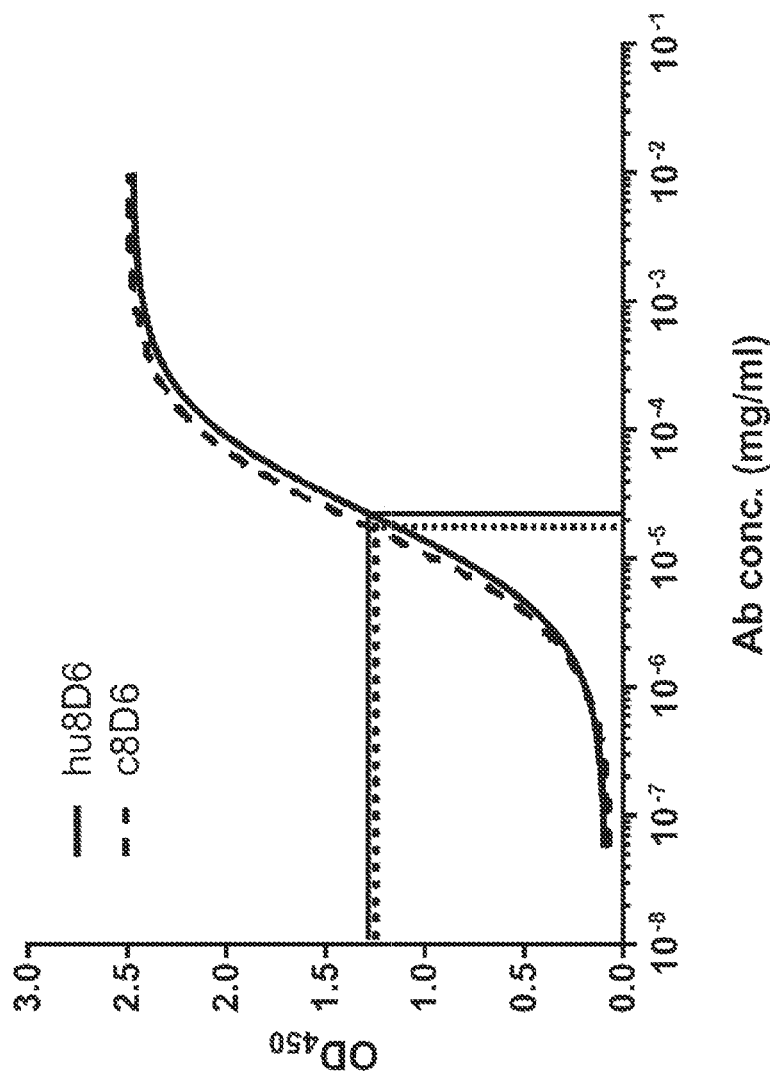
FIG. 3 illustrates the titration curves of hu8D6 (solid line) and the parent c8D6 antibody (dot line) binding to human IgE by ELISA.

The present invention pertains to humanized antibodies that bind to (1) human IgE in its secreted free form, (2) to membrane-bound IgE on B lymphocytes, and to (3) IgE bound by CD23 on B cells and (4) by free CD23 in solution. The anti-IgE antibodies do not bind to IgE bound by FcɛRI on mast cells and basophils and hence do not activate those inflammatory cells. In a broad definition, a humanized antibody is one in which the constant domains of the heavy and light chains and the framework regions of the $V_H$ and $V_L$ domains are of human origin.

Various methodologies employing phage, yeast, or ribosomes to display single-chain antibody libraries, which comprise the $V_H$ and $V_L$ segments of human B lymphocytes, have been used successfully for screening antibodies for human cell surface antigens or cellular factors. Such methodologies can also be employed to screen human antibodies with the unique set of IgE-binding specificities of the present invention. Alternatively, antibodies of the present invention may be obtained in transgenic mice which bear human immunoglobulin VH and VL gene pools.

As an example, the present invention provides the detailed description of the preparation of a humanized version of murine anti-IgE monoclonal antibody, 8D6, which possesses the above set of binding specificities. The present disclosure provides a humanized anti-human IgE antibody, hu8D6, comprising a heavy chain variable region (SEQ ID NO: 2) and a light chain variable region (SEQ ID NO: 4). The amino acid sequences of hypervariable regions of hu8D6 are identified as followed: CDR-H1 comprises GYTFNGYWMH (SEQ ID NO: 5); CDR-H2 comprises YINPTTGHTEYNQKFKD (SEQ ID NO: 6); CDR-H3 comprises ARQEYRHSWFAY (SEQ ID NO: 7); CDR-L1 comprises QSVDYDGDTY (SEQ ID NO: 8); CDR-L2 comprises AASNLDS (SEQ ID NO: 9); CDR-L3 comprises QQTNEDPWT (SEQ ID NO: 10).

The invention provides a humanized anti-human IgE antibody, hu8D6, wherein the binding activities of the antibody in its bivalent form to human IgE is $EC_{50}=\sim10^{-10}$ M. The affinity of the antibody in its monovalent Fab form to human IgE is $KD=\sim10^{-11}$ M.

In the following examples, the invention provides a humanized anti-IgE antibody, hu8D6, which is capable of binding to free human IgE (unbound by its two receptors), membrane-bound IgEs (long and short forms) on B lymphocytes, and CD23-bound IgE but incapable of binding to FcɛRI-bound IgE and inducing-hexosaminidase release from mast cells or basophils. Besides, hu8D6 is able to efficiently inhibit the binding of IgE to FcɛRI. The immune complex of hu8D6 and human IgE is capable of binding to CD23, but incapable of binding to FcɛRI and inducing-hexosaminidase release from mast cells or basophils. Furthermore, hu8D6 can bind both membrane-bound IgE and crosslink CD23-bound IgE on B cells and hence can inhibit the de novo synthesis of IgE production from human peripheral mononuclear cells in an in vitro culture system.

In one aspect, the humanized anti-IgE antibody, hu8D6, can be a full-length antibody (e.g., an IgG molecule), an antigen-binding fragment (e.g., Fab or F(ab')$_2$), or a single-chain Fv.

In another aspect, the present humanized anti-IgE antibody, hu8D6, exhibits therapeutic properties and provides the method for treating IgE-mediated diseases, comprising administering to a patient in need thereof of an effective amount of the humanized anti-IgE antibody described herein either the antibody or the antigen-binding fragment. IgE-mediated diseases include allergic asthma, allergic rhinitis, atopic dermatitis, food allergy, chronic spontaneous (idiopathic) urticaria, chronic rhinosinusitis, systemic mastocytosis, cutaneous mastocytosis, allergic bronchopulmonary aspergillosis, recurrent idiopathic angioedema, and eosinophil-associated gastrointestinal disorder. It is noted that some of those diseases, such as chronic spontaneous urticaria, systemic mastocytosis, and recurrent idiopathic angioedema, are not allergic diseases and do not involve external allergens.

Example 1 Generation of a Humanized Anti-IgE Antibody

CDR Grafting

The amino acid sequence of $V_H$ (SEQ ID NO: 1) and Vκ (SEQ ID NO: 3) domains from 8D6 were aligned with those of the human germline $V_H$1-69/JH4 and Vκ1-39/Jκ1 alleles. To make the CDR graft, the acceptor $V_H$ framework, which differs from the human germline $V_H$1-69 allele at 4 positions M48I, R66K, V67A, and S76N, was used. The CDRs, which are position 26-35 (CDR-H1, SEQ ID NO: 5), 50-56

(CDR-H2, SEQ ID NO: 6), and 93-104 (CDR-H3, SEQ ID NO: 7) of 8D6 were engineered into the acceptor $V_H$ framework to generate a direct CDR-graft of 8D6 $V_H$ as shown in FIG. 1. In the Vκ domain, the CDRs of positions 27-34 (CDR-L1, SEQ ID NO: 8), 50-56 (CDR-L2, SEQ ID NO: 9), and 89-97 (CDR-L3, SEQ ID NO: 10) were grafted to the acceptor Vκ framework, which differs from the human germline Vκ1-39 allele at a position M4L (FIG. 2). The direct CDR-graft of 8D6 $V_L$ was referred to as hu8D6 $V_L$ (SEQ ID NO: 4).

IgG Production

In order to obtain humanized 8D6 (hu8D6) and chimeric 8D6 (c8D6) antibodies, the Expi293™ expression system (Invitrogen) was used for transient expression. Transfection was performed in 30 mL culture in 125 mL flasks using ExpiFectamine™ 293 reagent (Invitrogen). One day prior to transfection, Expi293F™ cells were diluted with Exppi293™ Expression medium (Invitrogen) to a density of $2 \times 10^6$ cells/mL. On the day of transfection, cultures were counted and concentrated to $2.5 \times 10^6$ cell/mL by centrifuging, removing old media, and adding fresh medium. Transfection complexes were made by diluting 80 μL of ExpiFectamine 293 into 1.5 mL of OPTI-MEM (Invitrogen) and 5 minutes alter adding the diluted ExpiFectamine 293™ solution to 30 μg plasmid DNA. 3 mL DNA-transfection reagent complex solution were then incubated at room temperature for 20 minutes and slowly added to the suspension culture while slowly swirling the flask. The transfected cells were placed back on the orbital shaker in a 37° C. incubator and incubated for 16 hours. After incubation, 150 μL of ExpiFectamine 293™ Transfection Enhancer 1 and 1.5 mL of ExpiFectamine 293™ Transfection Enhancer 2 were added to the culture. The cultures were ended at day 7 post-transfection and harvested for antibody purification. Antibodies were purified from the supernatants using rProtein-A Sepharose™ affinity chromatography (GE Healthcare). The final product was homogenous as determined by size exclusion fast protein liquid chromatography with >99% of the protein eluting as a single peak of about $M_r$ 150,000.

Binding Analysis (EC50)

The Fc region of human IgE (ε.Fc 2-4), which starts at $Ser^{226}$ to $Gly^{599}$ according to the numbering system as previously described by Wan et al. (*Nature Immunol.*, 2002, 3:681-686) and contains two mutations N265Q and N371Q, was expressed in Expi293F™ cells and purified by anti-IgE immunoaffinity chromatography using Omalizumab-coupled NHS-activated Sepharose™ resin (GE Healthcare). For $EC_{50}$ determination of hu8D6, ε.Fc 2-4 protein was immobilized on 96-well plates at 50 ng/well in coating buffer (15 mM $Na_2CO_3$, 35 mM $NaHCO_3$, pH 9.6) and incubated at 4° C. overnight. Coated wells were blocked by 200 μL/well of assay diluents (0.5% BSA, 0.05% Tween-20, 0.01% thimerosal in PBS) at room temperature for 1 hour. Plates were washed 3 times with 200 μL/well of wash buffer (PBS with 0.05% Tween-20). 100 μL of antibody diluents (serially diluted from 0.1 mg/ml in 1:3 steps) were added to coated wells. The incubation was carried out at room temperature for 2 hours. All wells were aspirated and washed 6 times with 200 μL/well of wash buffer. The plates were incubated with a 1:10,000 dilution of horse radish peroxidase (HRP)-conjugated goat anti-murine IgG-Fc antibody (Jason ImmunoResearch) for 1 hour (100 μL/well). Then all wells were washed six times with 200 μL/well of wash buffer. Finally, wells were developed by 50 μL/well of NeA-Blue TMB substrate (Clinical Science Products) and the reaction was stopped by addition of 50 μL/well of 1N HCl. The absorbance was measured at $OD_{450}$ on an ELISA reader. The $EC_{50}$ was calculated using the Prism software (GraphPad). As shown in FIG. 3, the $EC_{50}$ of hu8D6 and c8D6 were $1.48 \times 10^{-10}$ and $1.16 \times 10^{-10}$ M. The results indicate that the binding activity of hu8D6 was almost completely preserved after CDR grafting process.

Competition Analysis (IC50)

Figure 4:
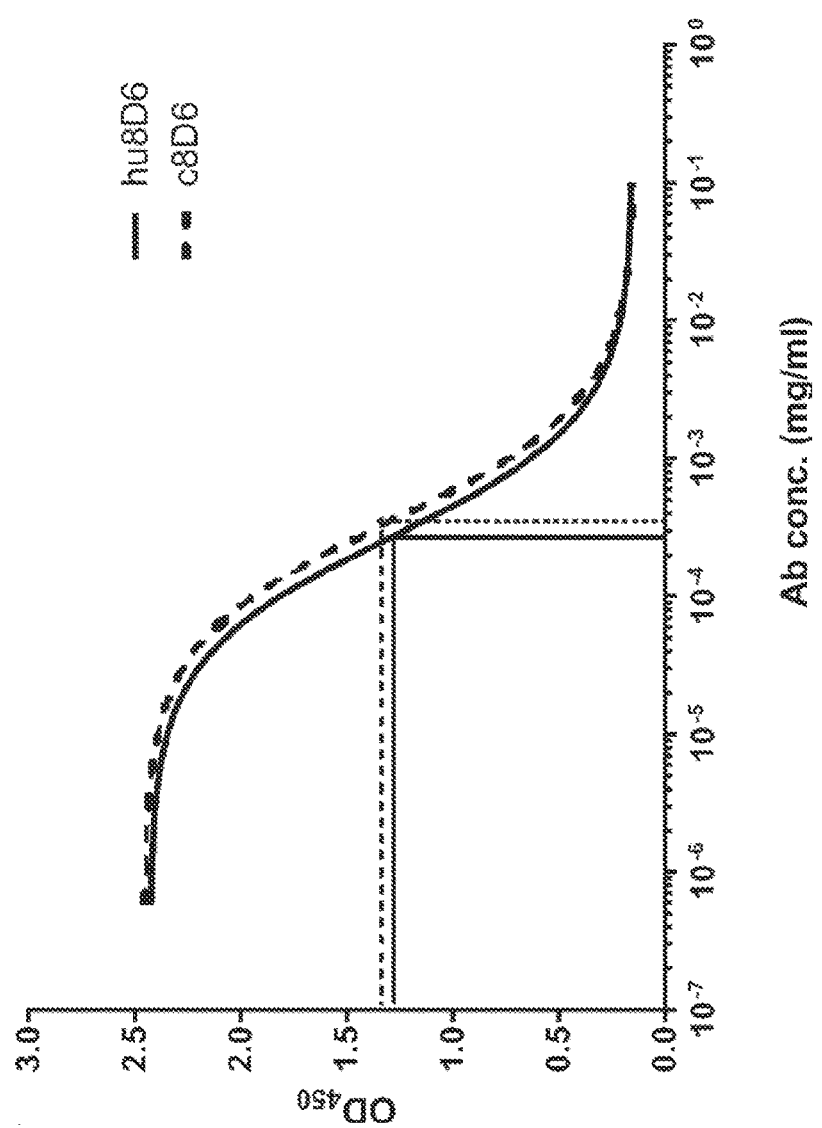
FIG. 4 illustrates the inhibitory curves of hu8D6 (solid) and chimeric 8D6 (c8D6, dot line) to compete with HRP-conjugated c8D6 to bind human IgE by ELISA.

Competitive ELISA tests were performed to compare the effectiveness of hu8D6 and c8D6 to compete with HRP-conjugated c8D6 in binding to human IgE to determine the binding property of hu8D6. The wells of ELISA plates were coated with 50 ng of ε.Fc 2-4 protein in coating buffer overnight at 4° C. and blocked by incubating with assay diluents. Separately, a stock solution of HRP-c8D6 was diluted 1:1,000 in assay diluents and aliquots were mixed with unconjugated c8D6 or hu8D6 serially diluted from 0.1 mg/ml in 1:3 steps. Both series of mixtures were added to the ELISA wells and incubated for 1 hour at room temperature. The wells were then washed with PBST, incubated with TMB, and their $OD_{450}$. The $IC_{50}$ was calculated using the Prism software. The $IC_{50}$ of unconjugated hu8D6 and c8D6 were $1.79 \times 10^{-9}$ and $2.28 \times 10^{-9}$ M as shown in FIG. 4. The results indicated that the hu8D6 bound to an identical epitope to 8D6.

KD Determination by Surface Plasmon Resonance (SPR) Analysis

To produce hu8D6 Fab, cDNAs of $V_H$ and $V_k$ DNA segments of hu8D6 antibody were respectively joined to a human C 1-CH1 domain and a human C region of an Fab expression vector that was modified from the pIgG1( ) vector by replacing the entire C 1 constant region with the C 1-CH1 domain (Chen et al. *J Immunol.* 184:1748-1756). The Expi293™ expression system (Invitrogen) was used for transient expression. Hu8D6 Fabs was purified from the supernatants using KappaSelect Sepharose™ affinity chromatography (GE Healthcare). The final product was homogenous as determined by size exclusion fast protein liquid chromatography with >99% of the protein eluting as a single peak of about $M_r$ 50,000.

Figure 5:
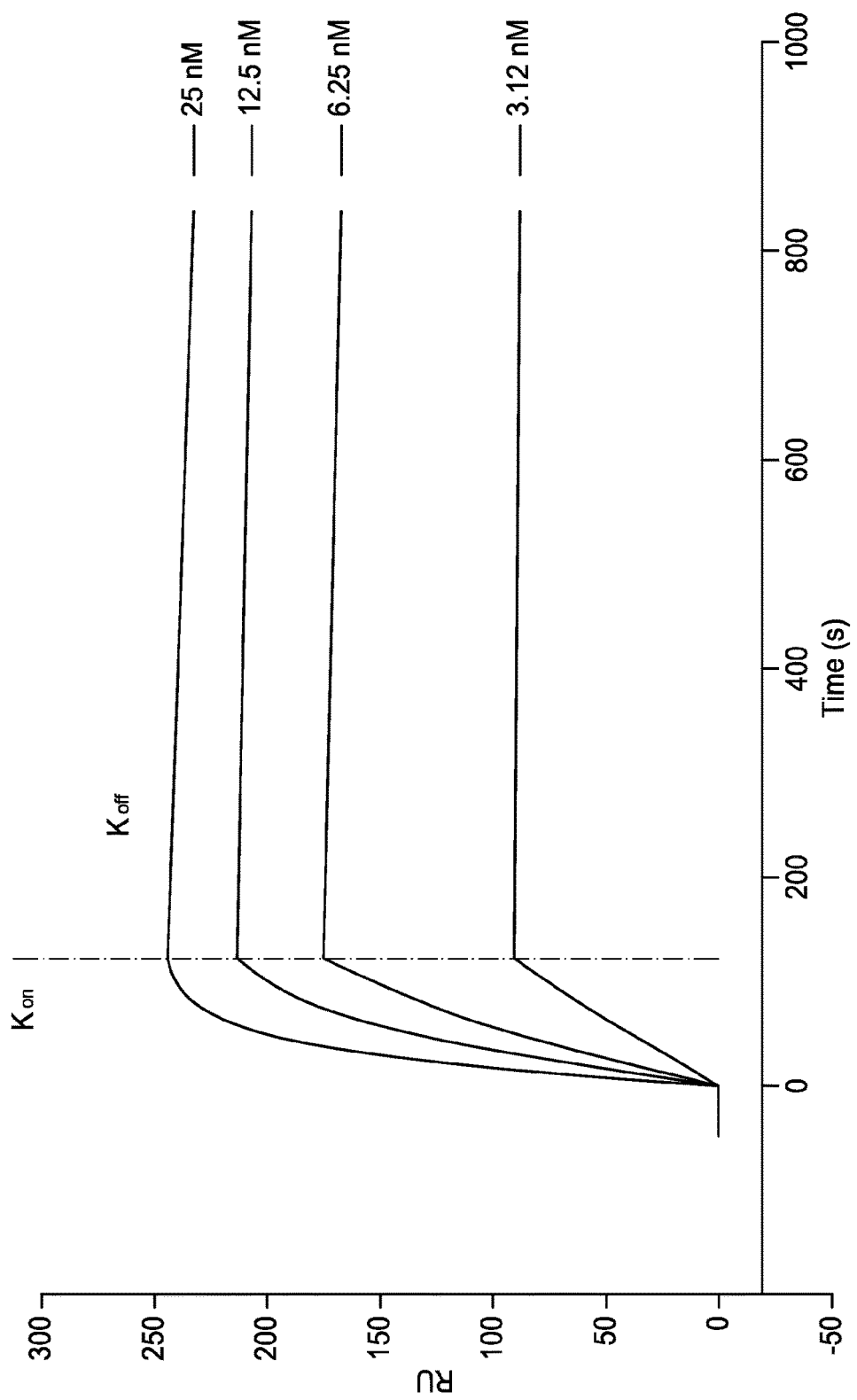
FIG. 5 illustrates the surface plasmon resonance (SPR) curves of hu8D6 Fab to human IgE by BIAcore analysis. RU: response unit.

For KD determination of hu8D6, SPR assays were performed with a Biacore X instrument (GE Healthcare). Hu8D6 Fab was immobilized on a CM5 chip (GE Healthcare) by using an amine coupling kit (GE Healthcare). Coupling density was limited to <500 resonance units. ε.Fc 2-4 protein was injected over the sensor chip at concentrations of 25, 12.5, 6.25 and 3.125 nM in HBS-P buffer (GE Healthcare) at a flow rate of 30 μl $min^{-1}$. All samples were injected onto the flow cell for 120 s with a dissociation time of 720 s at 25° C. Regeneration of the sensor surface was performed with two 30-second injection of 10 mM glycine-HCl (pH 2.5). The sonograms of ε.Fc 2-4, at different concentrations, binding to immobilized hu8D6 Fab were shown in FIG. 5. Affinity and rate constants were calculated by using BIAevalution software (GE Healthcare), showing that the $k_{on}$ and $k_{off}$ of hu8D6 Fab to ε.Fc 2-4 are $1.23 \pm 0.17 \times 10^6$ $M^{-1}s^{-1}$ and $5.79 \pm 0.03 \times 10^{-5}$ $s^{-1}$, resulting in that the KD of hu8D6 is $4.8 \pm 0.7 \times 10^{-11}$ M.

FACS Analysis

Figure 6A:
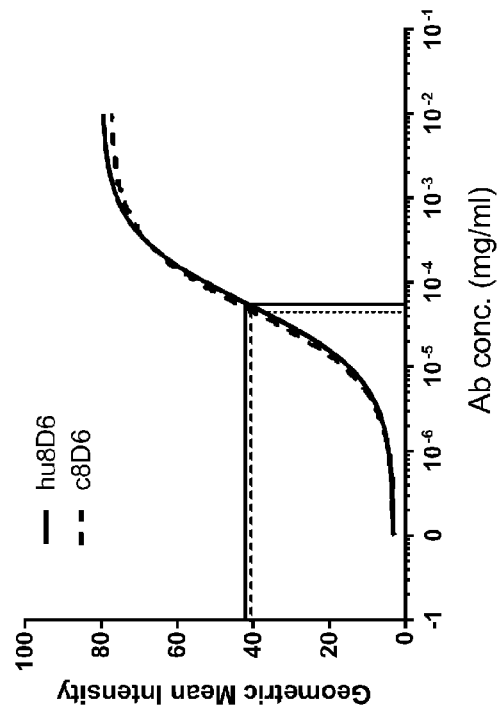
FIGS. 6a and 6b illustrate the binding of hu8D6 and c8D6 to mIgE.Fc-expressing Ramos cell lines by flow cytometric analysis. mIgE.Fc$_L$ Ramos: Ramos cells expressing the long form of human membrane-bound IgE.Fc (FIG. 6a); mIgE.Fc$_S$ Ramos: Ramos cells expressing the short form of human membrane-bound IgE.Fc (FIG. 6b).
Figure 6B:
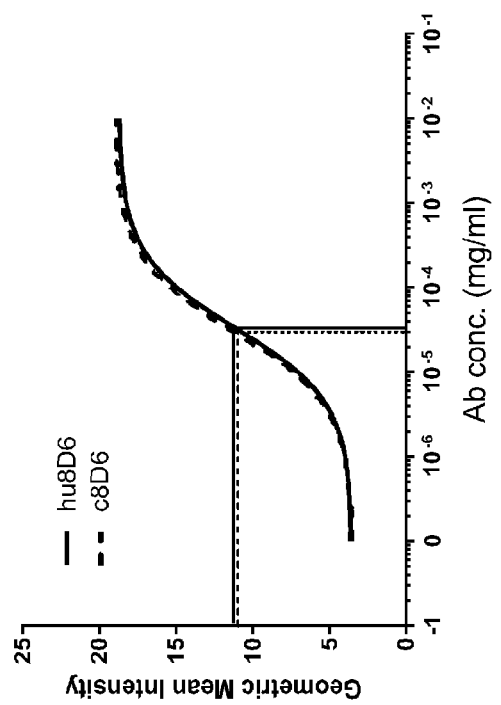

Ramos cell lines that were transfected with either recombinant DNA encoding $mIgE.Fc_L$ ($C_H2$-cytoplasmic tail of the long form of membrane ε chain) or $mIgE.Fc_S$ ($C_H2$-cytoplasmic tail of the short form of membrane ε chain) were generated by Chen et al. (Chen et al. *J Immunol.* 184:1748-1756) and used to determine binding activity of hu8D6. Ramos cells expressing $mIgE.Fc_L$ or $mIgE.Fc_S$ were resuspended in FACS buffer (1% FBS and 0.1% sodium azide in 1×PBS) at a cell density of $2 \times 10^6$ cells/mL. $2 \times 10^5$ cells in 100 µL of FACS buffer were incubated with hu8D6 or c8D6 at the concentration of 10, 1, 0.1, 0.01 and 0.001 µg/mL, for 30 minutes on ice, followed by washing with FACS buffer. Bound antibodies were detected by FITC-labeled goat IgG specific for human IgG-Fc (Caltag Laboratories). The stained cells were analyzed on a FACS Canto II flow cytometer (BD Biosciences). The geometric means of fluorescence intensity for the binding of antibodies to Ramos cell lines were analyzed using the FCSExpress software (DeNono software). The $EC_{50}$ was calculated using the Prism software. As shown in FIGS. 6a and 6b, The $EC_{50}$ of hu8D6 and c8D6 to bind to mIgE.$Fc_L$-expressing Ramos cells were $2.21\times10^{-10}$ and $2.0\times10^{-10}$, and the $EC_{50}$ of hu8D6 and c8D6 to mIgE.$Fc_S$-expressing Ramos cells were $3.86\times10^{-10}$ and $3.0\times10^{-16}$. The results indicated that the binding activities of hu8D6 and c8D6 to two mIgE isoforms were approximately equal.

Example 2 Inability of hu8D6 to Bind to Human FcεRI-Bound IgE

Inability of hu8D6 to Bind to IRE-Saturated Recombinant Chain of Human FcεRI

Figure 7:
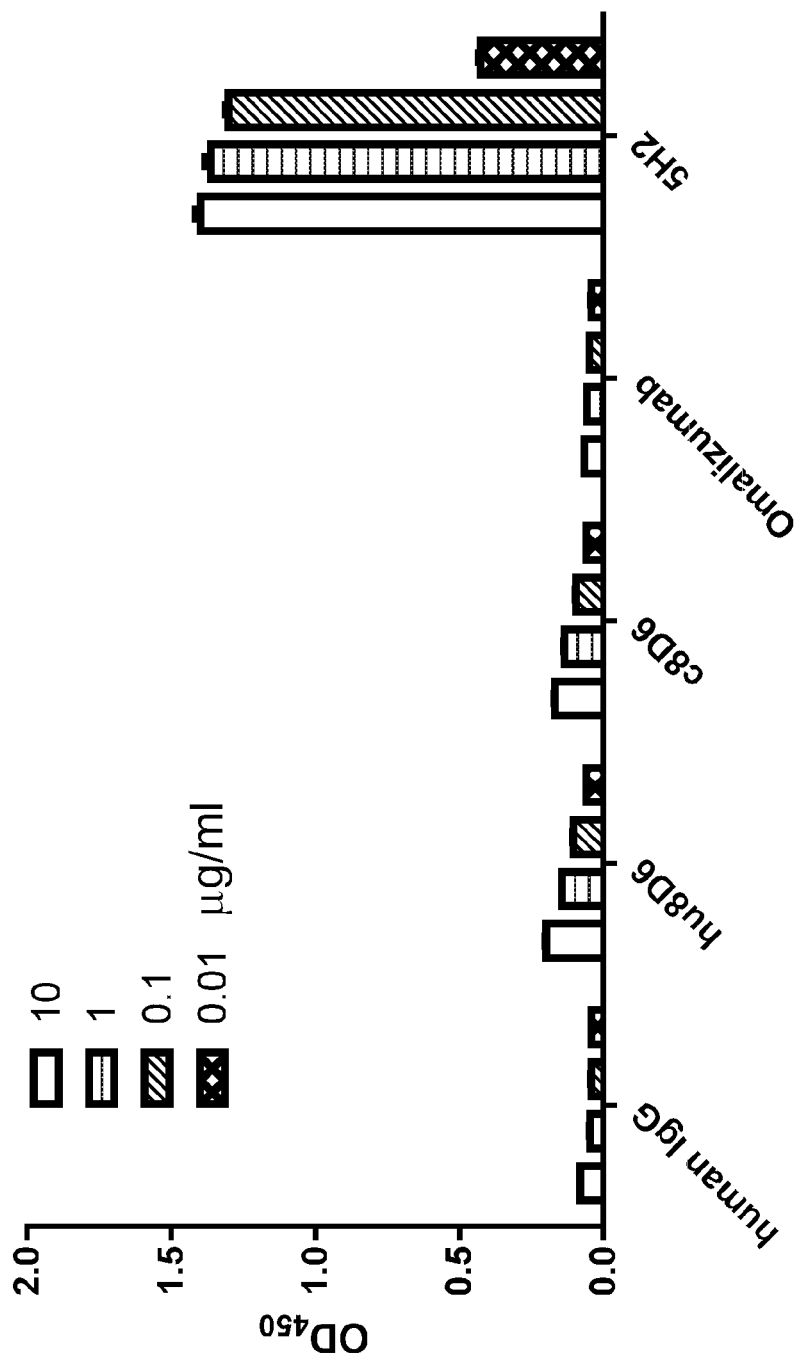
FIG. 7 illustrates the binding of hu8D6 to IgE-saturated recombinant a chain of human FcɛRI.
Figure 8:
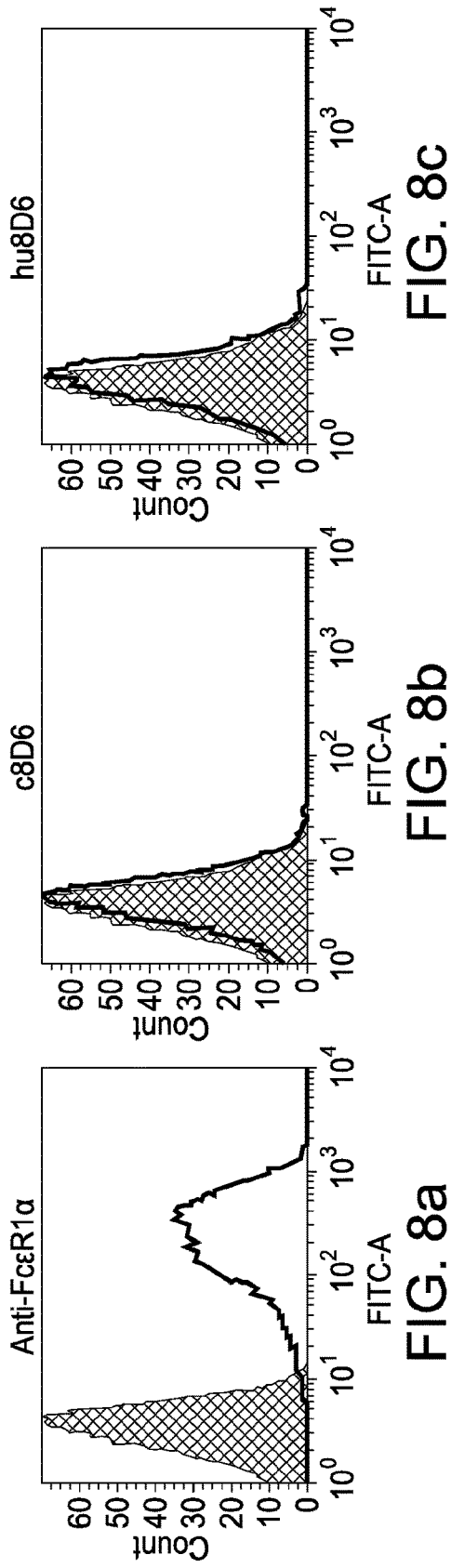
FIGS. 8a to 8e illustrate the binding of hu8D6 to human FcɛRI-expressing RBL SX-38 cells that were pre-loaded with human IgE.

ELISA was used to determine the binding of hu8D6 to solid-phase recombinant FcεRIα fusion protein (huFcεRIα-huFcγ1, referred to FcεRIα-Fc), which was composed of the extracellular region of human FcεRIα (from $Val^{26}$ to $Leu^{204}$) and the hinge-$C_H2$-$C_H3$ portion of human γ1 (Shiung et al., *Immunobiology*, 2012, 217:676-683). The FcεRIα-Fc protein was expressed by the FreeStyl™ 393F system (Invitrogen) and purified by protein A chromatography. The wells of ELISA plates were coated with 2 µg/mL of FcεRIα-Fc in coating buffer at 4° C. overnight and treated with assay diluents (0.5% BSA, 0.05% Tween-20, 0.01% thimerosal in PBS) for 1 hour at room temperature. The coated FcεRIα-Fc proteins were then saturated with 1 µg/mL IgE, which was purified from the culture medium of U266 cells by anti-IgE chromatography. After the wells were washed 6 times with wash buffer, the captured IgE was incubated with human IgE (Sigma), hu8D6, c8D6, Omalizumab and a murine anti-human IgE mAb 5H2 (AbD Serotec) at 10, 1, 0.1, and 0.01 µg/mL. The bound human IgE and murine IgG were detected using HRP-conjugated goat anti-human kappa light chain (GeneTex) and HRP-conjugated goat anti-murine IgG.Fc (Jackson ImmunoResearch). Humanized 8D6, c8D6, and Omalizumab were not bound to IgE-saturated recombinant FcεRIα fusion protein, while 5H2 did do so at all concentrations as shown in FIG. 7.

Inability of hu8D6 to Bind to IRE on Basophils

RBL SX-38 cells, rat basophilic leukemia cells transferred with genes encoding the α, β, and γ chains of human FcεRI (Wiegand et al., *J. Immunol.*, 1996, 157:221-230) were used as a pool of cell surface FcεRI. $2\times10^6$ RBL SX-38 cells in 1 mL of FACS buffer were incubated with IgE at the concentration of 3 µg/mL for 30 minutes on ice. The cells were washed with FACS buffer to remove unbound IgE and then 2×105 cells in 100 ml FACS buffer were incubated with hu8D6, c8D6, Omalizumab, and 5H2 antibody at the concentration of 10 µg/mL for 30 minutes on ice, followed by washing with FACS buffer. Bound antibodies were detected by FITC-labeled goat IgG specific for human IgG-Fc or FITC-labeled F(ab)'2 rabbit anti-murine IgG (AbD Serotec). The stained cells were analyzed on FACS Canto II. As shown in FIGS. 8a to 8e, humanized 8D6, c8D6, and Omalizumab could not bind to IgE-saturated RBL SX-38 cells, and 5H2 was bound to RBL SX-38 cells.

Competitive Analysis to FcεRIα-Fc Protein

Figure 9:
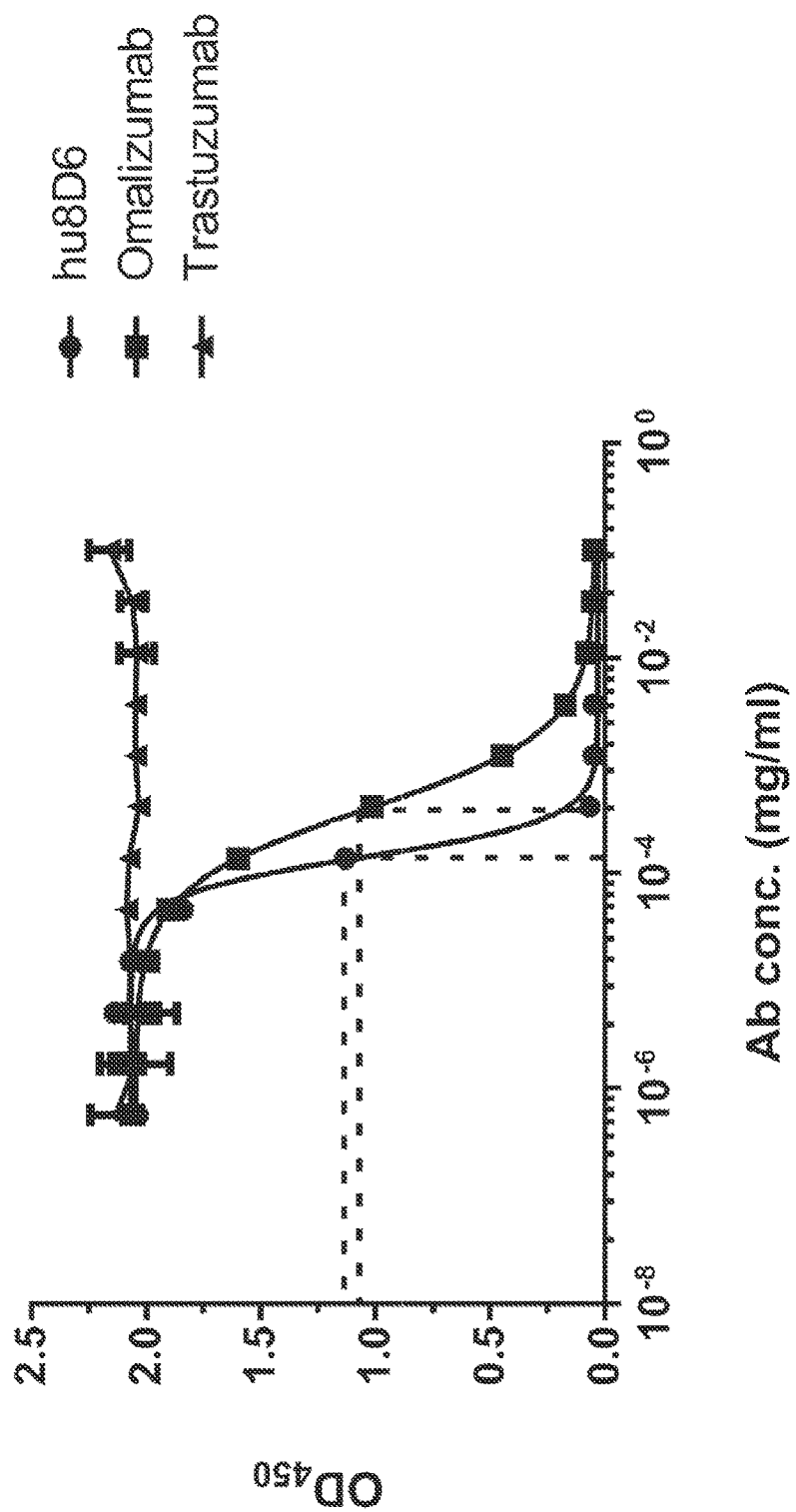
FIG. 9 illustrates the inhibitory curves of hu8D6 and Omalizumab to compete with recombinant FcɛRIa-Fc protein to bind human IgE by ELISA.

Competitive ELISA tests were performed to compare the effectiveness of hu8D6 and Omalizumab to compete with HRP-conjugated IgE in binding to FcεRIα-Fc protein (Shiung et al). The wells of ELISA plates were coated with 100 ng of U266 IgE protein in coating buffer overnight at 4° C. and blocked by incubating with assay diluents (0.5% BSA, 0.05% Tween-20, 0.01% thimerosal in PBS). Separately, a stock solution of HRP-IgE was diluted 1:6000 in assay diluents and aliquots were mixed with unconjugated hu8D6 or Omalizumab serially diluted from 0.1 mg/ml in 1:3 steps. Both series of mixtures were added to the ELISA wells and incubated for 1 hour at room temperature. The wells were then washed with PBST, incubated with TMB, and their $OD_{450}$. The $IC_{50}$ was calculated using the Prism software. Trastuzumab (Herceptin™), which targets human HER2 protein as a negative control, did not inhibit the binding of IgE to FcεRIα-Fc. The $IC_{50}$ of hu8D6 and Omalizumab to inhibit IgE binding to FcεRIα-Fc were 9.4 and $25.9\times10^{-10}$ M as shown in FIG. 9, indicating that hu8D6 is superior to Omalizumab in inhibiting the binding of IgE to its receptor.

Figure 10:
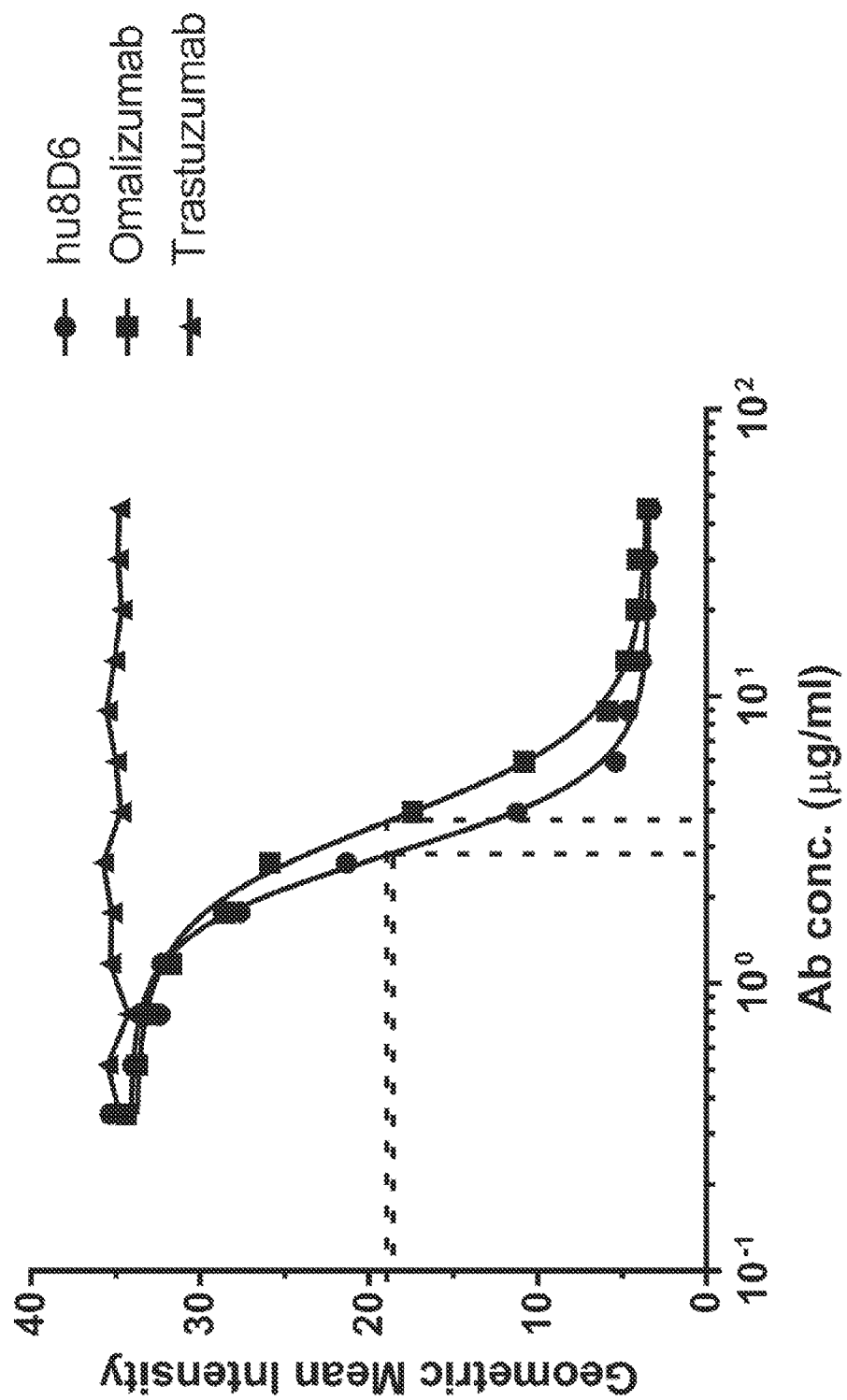
FIG. 10 illustrates the inhibitory curves of hu8D6 and Omalizumab to compete with native FcɛRI receptor on RBL SX-38 cells for human IgE binding by flow cytometric analysis.

Competitive Analysis to Cell Surface FcεRI $2\times10^5$ RBL SX-38 cells in 0.1 mL of FACS buffer were incubated with hu8D6, Omalizumab or Trastuzumab at different concentrations of 45, 30, 13.3, 8.9, 5.93, 3.95, 2.63, 1.76, 1.17, 0.78, 0.52 and 0.35 µg/mL as well as FITC-labeled IgE (4.5 µg/mL) for 30 minutes on ice. The cells were washed with FACS buffer to remove unbound IgE. The stained cells were analyzed on FACS Canto II. The $IC_{50}$ was calculated using the Prism software. Trastuzumab did not affect the binding of IgE to SX-38 cells. The $IC_{50}$ of hu8D6 and Omalizumab to inhibit IgE binding to SX-38 cells were $18.8\times10^{-9}$ and $24.7\times10^{-9}$ M as shown in FIG. 10, indicating that hu8D6 is superior to Omalizumab in inhibiting the binding of IgE to FcεRI-expressing cells.

Example 3 Inability of hu8D6 to Sensitize RBL SX-38 Cells

The extent of degranulation was assessed by measuring the release of β-hexosaminidase, a lysosomal enzyme stored in granules, into the culture medium. RBL SX-38 cells were seeded in a 24-well plate at $3\times10^5$ cells/well in 0.5 mL of culture medium overnight in at 37° C. On the next day, the medium was removed and 0.25 mL of pre-warmed culture medium containing 1 µg/mL human IgE was added to each well. After 2 hour of incubation in a 37° C. incubator, each well was washed twice with 0.5 mL of Tyrode's buffer (135 mM NaCl, 5 mM KCl, 5.6 mM glucose, 1.8 mM $CaCl_2$, 1 mM $MgCl_2$, 20 mM HEPES, and 0.5 mg/mL BSA, pH 7.3) and then 0.25 mL of pre-warmed Tyrode's buffer containing 10, 1, 0.1, or 0.01 µg/mL of antibodies or 1% Triton X-100 added. After a 30 minutes incubation in a 37° C. incubator, the supernatants were collected and centrifuged at 300×g for 5 minutes at room temperature and 50 µL clear supernatants were transferred from each well to that of a new 96 well black OptiPlate™ (Perkin-Elmer). 50 mL of substrate solution (80 µM of 4-MUG (4-methylumbelliferyl-N-acetyl-d-glucosaminide), Sigma) in 0.1 M citric acid buffer (pH 4.5) was added to each well and the plate was incubated at 37° C. for 1 hour. The reaction was terminated by adding 100 µL glycine buffer (0.2 M glycine, 0.2 M NaCl, pH 10.7). The resulting fluorescence (excitation 355 nm; emission 460 nm) was measured at the top of each well by a Victor™ 3 fluorescence reader (Perkin-Elmer). Measured values were expressed as percentages relative to the value of release (100%) obtained by lysing cells with 1% Triton X-100.

Figure 11:
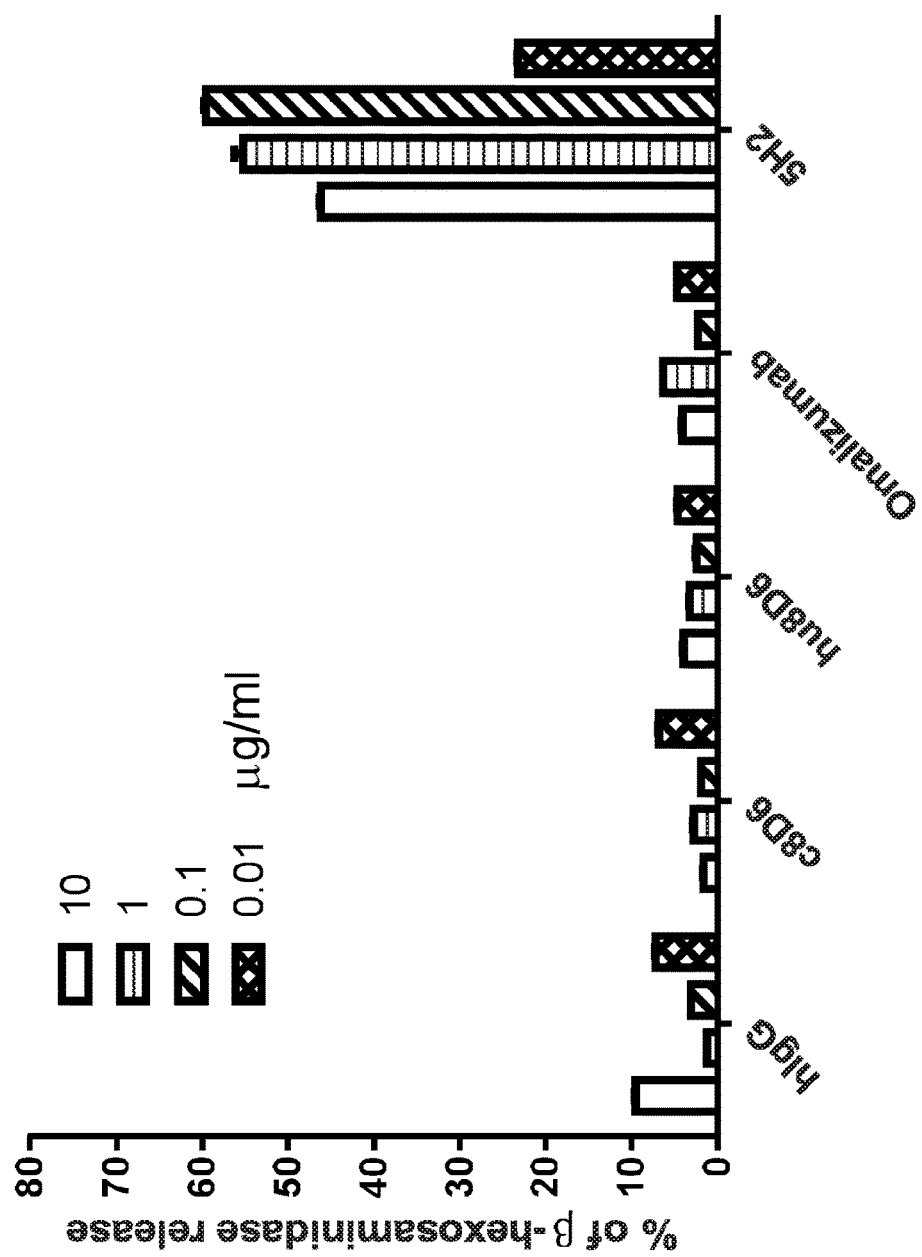
FIG. 11 illustrates the inability of hu8D6 to activate and trigger the degranulation of IgE-sensitized RBL SX-38 cells.

Humanized 8D6, c8D6, and Omalizumab did not induce the degranulation of IgE-sensitized RBL SX-38 cells, while 5H2 did so (FIG. 11).

Example 4 Ability of hu8D6 to Bind to Human CD23-Bound IgE

Ability of hu8D6 to Bind to IRE-Saturated Recombinant Trimeric Human CD23

Figure 12:
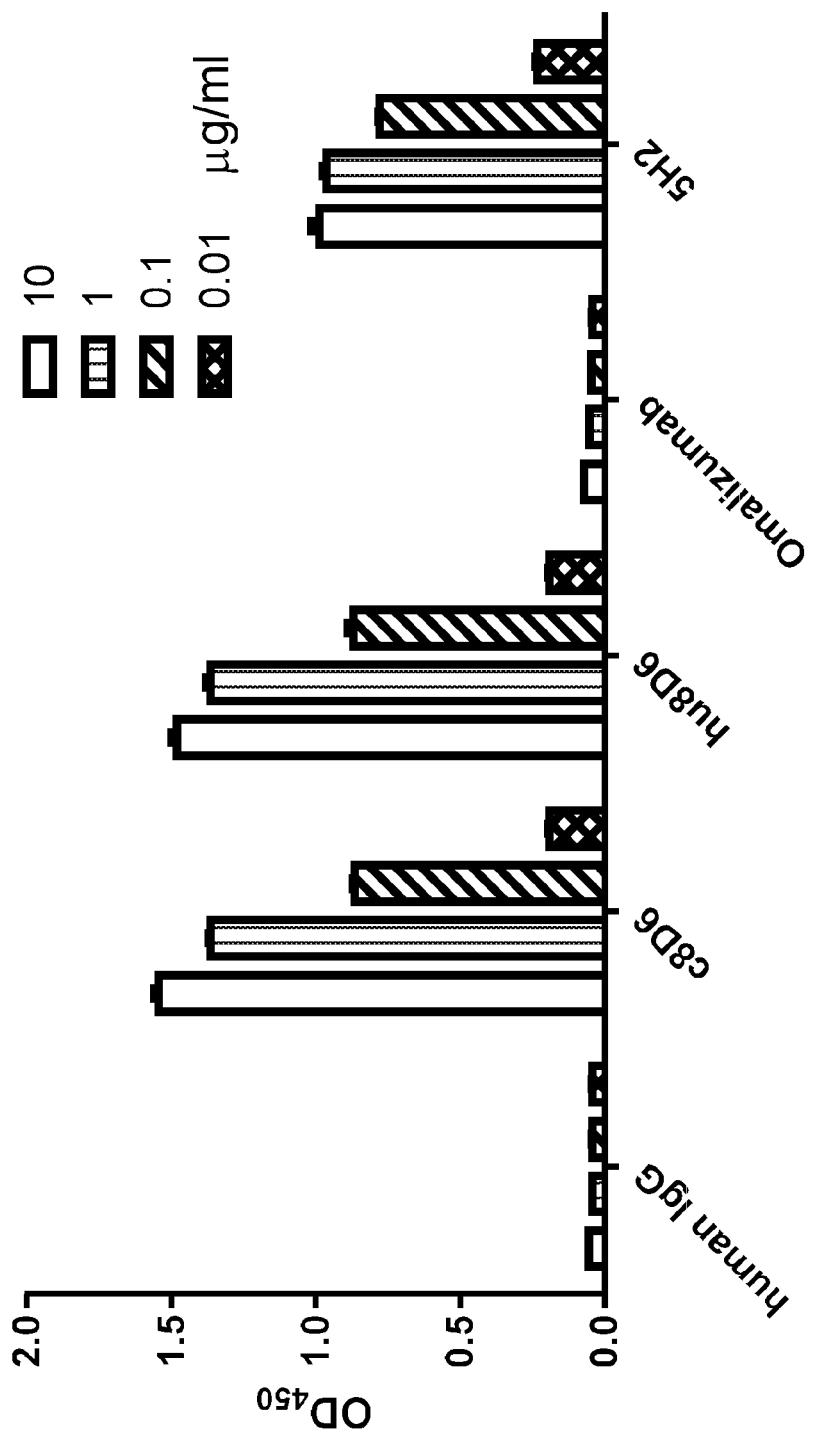
FIG. 12 illustrates the binding of hu8D6 to IgE-saturated recombinant trimeric human CD23.
Figure 13A:
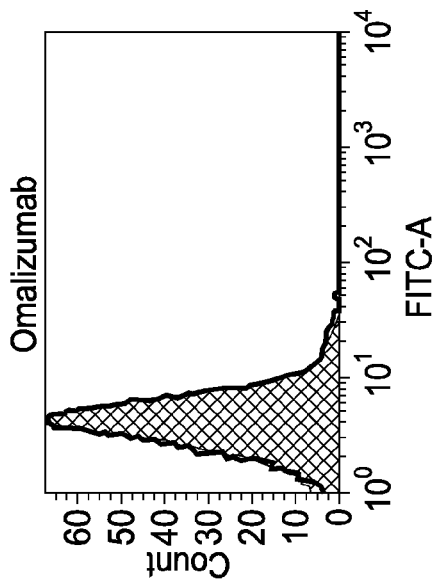
FIGS. 13a to 13d illustrate the binding of hu8D6 to human CD23-expressing SKW6.4 cells.
Figure 13B:
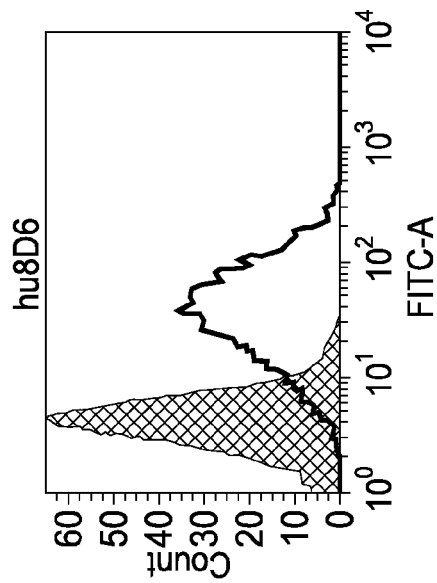
Figure 13C:
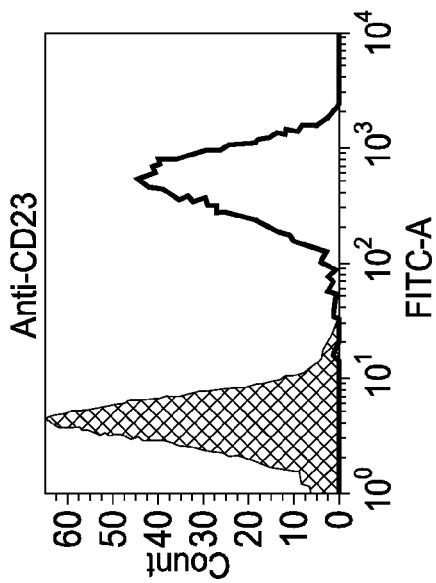
Figure 13D:
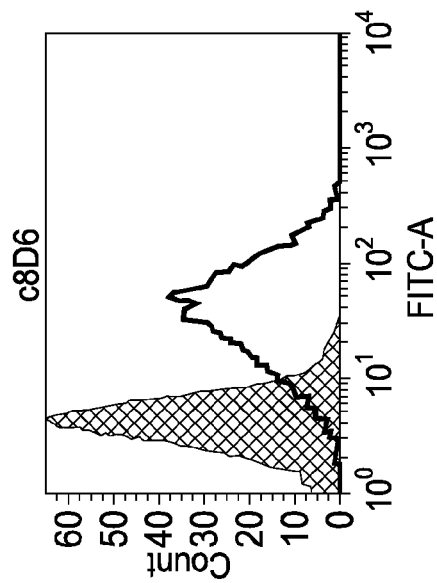

ELISA was used to determine the binding of hu8D6 to solid-phase recombinant human CD23 fusion protein (ILZ-CD23), which contains N-terminal isoleucine zipper (ILZ) and extracellular region ($Asp^{48}$ to $Ser^{321}$) of human CD23 and forms a non-covalent trimer through the ILZ motif (Shiung et al., *Immunobiology*, 2012, 217:676-683). The polyhistidine-tagged ILZ-CD23 was expressed by the FreeStyle™ 293F system, purified from the transfection culture medium using nickel Sepharose™ chromatography (GE Healthcare), and then preserved in 1×HBSS buffer with 2 mM $CaCl_2$. ELISA plates were coated with purified ILZ-CD23 at 5 µg/mL and blocked, and the coated ILZ-CD23 was then saturated with 3 µg/mL of purified human IgE in $Ca^{2+}/Mg^{2+}$ assay diluents (1 mM $CaCl_2$, 0.5 mM $MgCl_2$, 0.5% BSA, 0.05% Tween-20, and 0.01% thimerosal in PBS). After the wells were washed 6 times with wash buffer, captured IgE was then incubated with hu8D6, c8D6, Omalizumab and 5H2 at 10, 1, 0.1, and 0.01 µg/mL in $Ca^{2+}/Mg^{2+}$ assay diluents. The bound human IgG and murine IgG were detected using HRP-conjugated goat anti-human IgG.Fc and HRP-conjugated goat anti-murine IgG.Fc. Humanized 8D6, c8D6 and 5H2 antibody, could bind to human IgE-saturated recombinant CD23 coated on solid surface, while Omalizumab has no binding activity, comparable to the isotype-control human IgG antibodies as shown in FIG. 12.

Ability of hu8D6 to Bind to IRE-Pulsed SKW6.4 B Cells

A human B cell line expressing high level of CD23 (Pathan et al., Blood, 2008, 111:1594-1602) was used to pulse CD23 by incubating with IgE. $2\times10^6$ SKW6.4 cells in 1 mL of $Ca^{2+}/Mg^{2+}$ FACS buffer (1 mM $CaCl_2$, 0.5 mM $MgCl_2$, 1% FBS and 0.1% sodium azide in 1×PBS) were incubated with IgE at the concentration of 3 µg/mL for 30 minutes on ice. The cells were washed with $Ca^{2+}/Mg^{2+}$ FACS buffer incubated with hu8D6, c8D6, Omalizumab, and anti-CD23 antibody (Clone: EBVCS2, eBioscience) at the concentration of 10 µg/mL for 30 minutes on ice, followed by washing with $Ca^{2+}/Mg^{2+}$ FACS buffer. Bound antibodies were detected by FITC-labeled goat IgG specific for human IgG-Fc or FITC-labeled F(ab)'$_2$ rabbit anti-murine IgG. The stained cells were analyzed on a FACSCanto™ II flow cytometer. Anti-CD23 was found to bind well onto the skw6.4 B cells as a positive control. Omalizumab was prevented from binding to IgE bound by CD23, while hu8D6 and c8D6 were able to effectively bind to IgE on SKW6.4 cells as shown in FIGS. 13a to 13d.

Example 5 Inability of the Immune Complex of hu8D6 and IgE to Bind to Human FcεRI Preparation of the Immune Complex of hu8D6 and IRE
Purified human IgE (about 190 kDa), hu8D6, c8D6, Omalizumab, and 5H2 (about 150 kDa) were diluted to 1 mg/mL in 1×PBS. Mixtures containing anti-IgE:IgE immune complexes were prepared by mixing 95 µL of 1 mg/mL human IgE, 75 µL of 1 mg/mL anti-IgE mAbs. The mixtures were incubated for 2 hours at room temperature and used for further use.

Inability of the Immune Complex of hu8D6 and IRE to Bind to RBL SX-38 Cells $2\times10^5$ RBL SX-38 cells in 100 L FACS buffer were incubated with hu8D6:IgE, c8D6:IgE, Omalizumab:IgE, and 5H2:IgE immune complexes at the concentration of 10 µg/mL for 30 minutes on ice, followed by washing with FACS buffer. Bound antibodies were detected by FITC-labeled goat IgG specific for human IgG-Fc or FITC-labeled F(ab)'$_2$ rabbit anti-murine IgG. The stained cells were analyzed on a FACSCanto™ II flow cytometer. As shown in FIGS. 14a to 14e, the hu8D6:IgE, c8D6:IgE, and Omalizumab:IgE immune complexes were unable to bind to RBL SX-38 cells while as anti-FcεRI and 5H2:IgE did bind.

Figure 15:
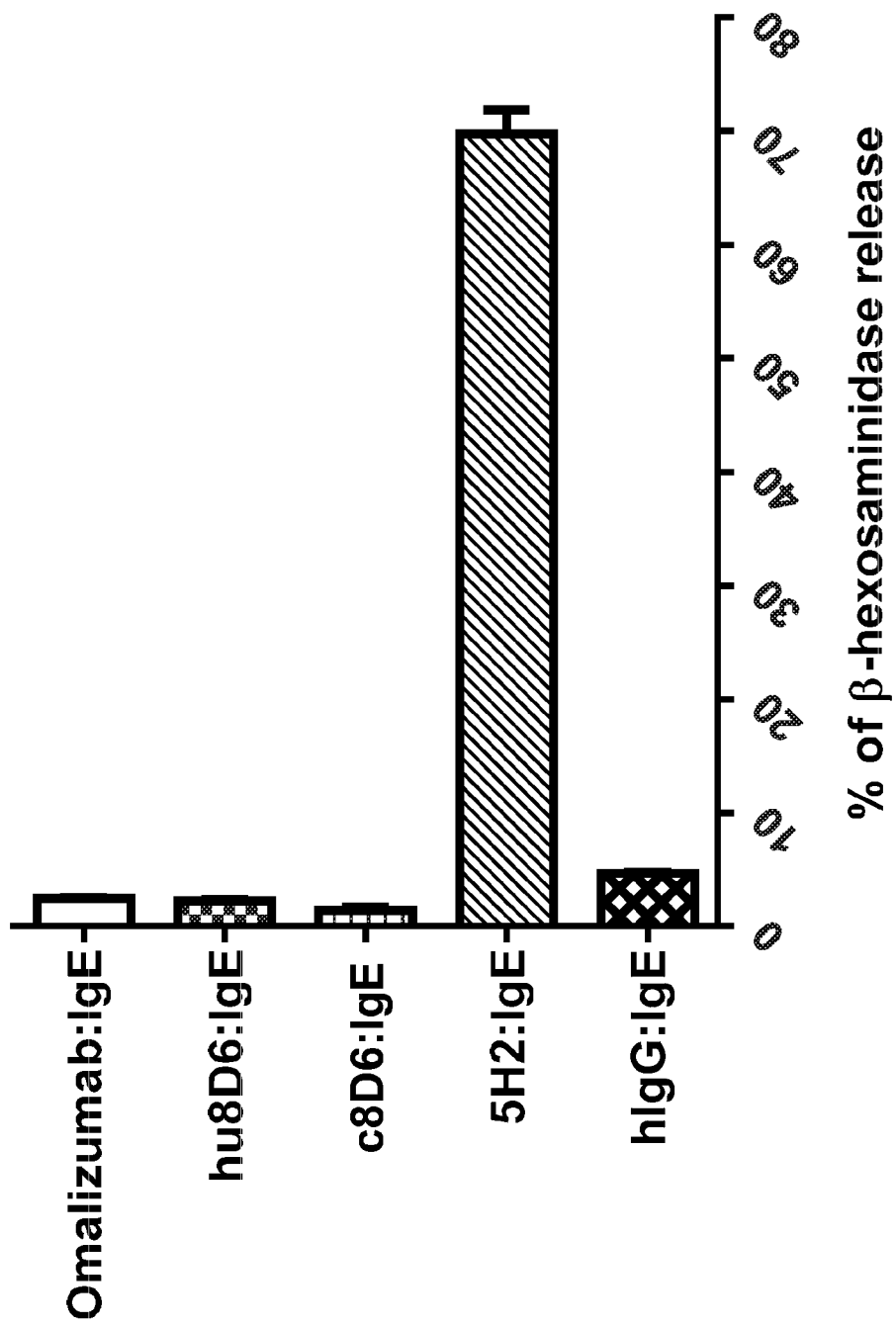
FIG. 15 illustrates the inability of the hu8D6:IgE immune complexes to activate and induce the degranulation of IgE-sensitized RBL SX-38 cells.
Figure 16A:
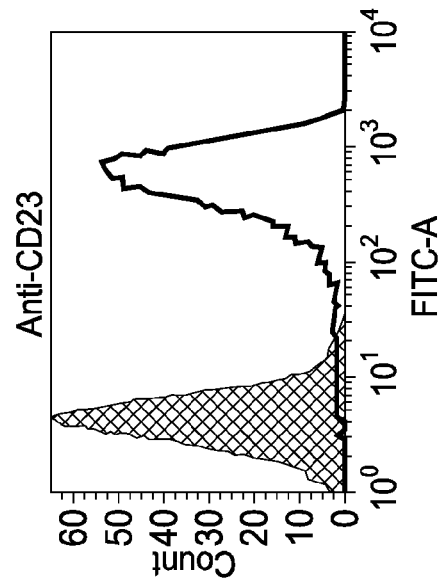
FIGS. 16a to 16d illustrate the binding of the hu8D6:IgE immune complexes to human CD23-expressing SKW6.4 cells.
Figure 16B:
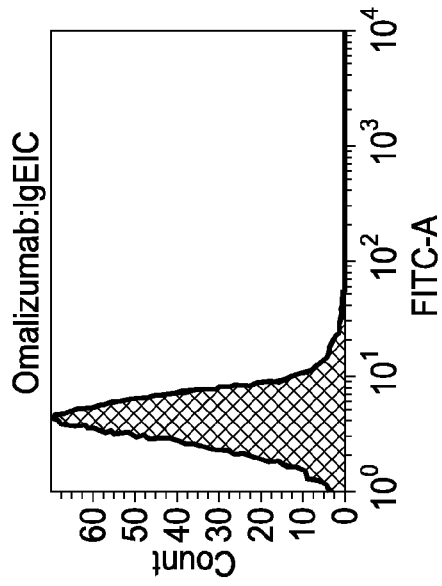
Figure 16C:
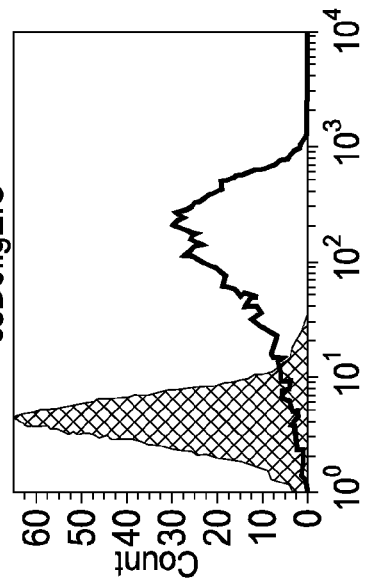
Figure 16D:
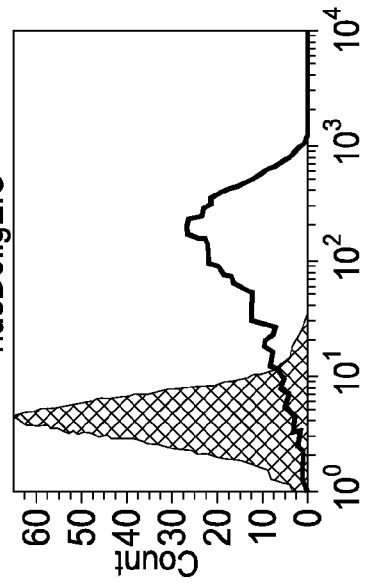

Inability of the Immune Complex of hu8D6 and IRE to Activate RBL SX-38 Cells $3\times10^5$ RBL SX-38 cells were seeded in a 24-well plate in 0.5 mL of culture medium overnight in a 37° C. incubator. On the next day, each well was washed twice with 0.5 mL of Tyrode's buffer and then 0.25 mL of pre-warmed Tyrode's buffer containing 10 µg/mL of the anti-IgE:IgE immune complexes or 1% Triton X-100 was added. After 30 minutes incubation at 37° C., the supernatants were collected and centrifuged at 300×g for 5 minutes at room temperature and 50 µL clear supernatant were transferred from each well to that of a new 96-well black OptiPlate™ (Perkin-Elmer). 50 µL of 4-MUG substrate solution was added into each well and the plate was incubated at 37° C. for 1 hour. The reaction was terminated by adding 100 µL glycine buffer. As shown in FIG. 15, the hu8D6:IgE, c8D6:IgE, and Omalizumab:IgE immune complexes did not induce the degranulation of RBL SX-38 cells while as 5H2:IgE did.

Example 6 Ability of the Immune Complex of hu8D6 and IgE to Bind to Human CD23

$2\times10^5$ SKW6.4 cells in 100 µL of $Ca^{2+}/Mg^{2+}$ FACS buffer were incubated with hu8D6:IgE, c8D6:IgE, Omalizumab:IgE immune complexes and anti-CD23 at the concentration of 10 µg/mL for 30 minutes on ice, followed by washing with $Ca^{2+}/Mg^{2+}$ FACS buffer. Bound anti-IgE:IgE immune complexes were detected by FITC-labeled goat IgG specific for human IgG-Fc or FITC-labeled F(ab)'$_2$ rabbit anti-murine IgG. The stained cells were analyzed on a FACS Canton™ II flow cytometer. As shown in FIGS. 16a to 16d, the Omalizumab:IgE immune complex was not able to bind to surface CD23, whereas hu8D6:IgE, c8D6:IgE immune complexes and anti-CD23 were able to effectively bind to SKW6.4 cells.

Example 7 Ability of hu8D6 to Inhibit IgE Production of PBMCs

Figure 17A:
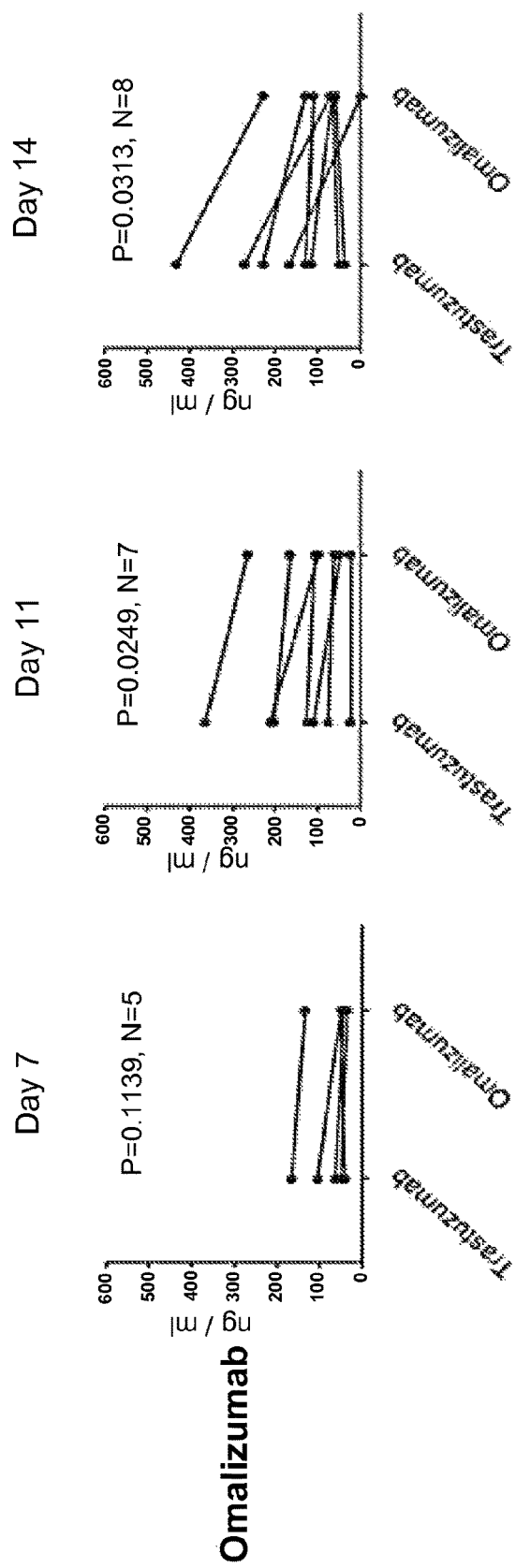
FIGS. 17a and 17b illustrate the inhibitory effects of Omalizumab (FIG. 17a) or hu8D6 (FIG. 17b) on de novo IgE synthesis in vitro.
Figure 17B:
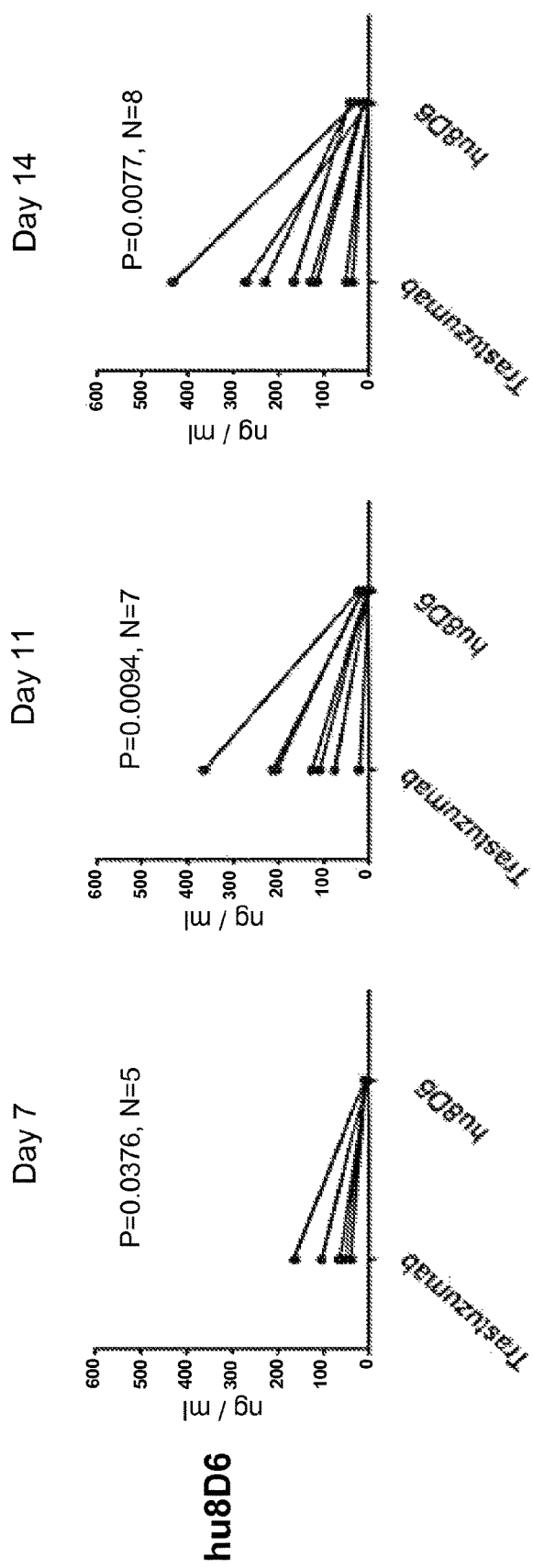

Peripheral blood mononuclear cells (PBMCs) were purified from blood samples from healthy donors or atopic patients by centrifugation over a Ficoll-Paque® PLUS (GE Healthcare) density gradient. The isolated PBMCs were suspended at $10^6$ cell/mL in complete IMDM medium (Invitrogen) with 100 ng/mL human IL-4 (R&D systems) and 100 ng/mL mouse anti-CD40 monoclonal antibody (BioLegend, clone: G28-5). Humanized 8D6, Omalizumab and Trastuzumab were added to the medium at a concentration of 10 µg/ml. After 7-, 11- and 14-day cultivation, cell-free supernatants were harvested and stored at −20° C. IgE released into the supernatants were measured by ELISA using anti-human IgE, HP6061 (Abcam), as capture antibody and biotin-labeled anti-human IgE, HP6029 (Abcam), as detection antibody. Briefly, the HP6061 was immobilized on 96-well plates at 100 ng/well in coating buffer (15 mM Na$_2$CO$_3$, 35 mM NaHCO$_3$, pH 9.6) and incubated at 4° C. overnight. Coated wells were blocked by 200 μL/well of assay diluents (0.5% BSA, 0.05% Tween-20, 0.02% ProClin 300 in PBS) at room temperature for 1 hour. Plates were washed 3 times with 200 μL/well of wash buffer (PBS with 0.05% Tween-20). Purified U266 IgE was used to generate a standard curve (range 800 to 3.125 ng/ml by 2-fold serial dilution). To improve the accuracy of IgE qualification, the IgE standards were prepared in complete IMDM medium and spiked with hu8D6, Omalizumab or Trastuzumab at 10 μg/ml. 100 μL of the clear supernatants and standards were added to coated wells. The incubation was carried out at room temperature for 1 hour. All wells were aspirated and washed 6 times with 200 μL/well of wash buffer. The captured IgE was incubated with 100 μL of detection antibody solution (50 ng/ml of biotin labeled HP6029 in assay diluent) at room temperature for 1 hour. Then, the bound biotin-HP6029 was detected using streptavidin poly-HRP (1:10,000 dilution, Thermo Pierce) for 1 hour (100 μL/well). All wells were aspirated and washed 6 times with 200 μL/well of wash buffer. Finally, wells were developed by 100 μL/well of NeA-Blue TMB substrate (Clinical Science Products) and the reaction was stopped by addition of 100 μL/well of 1M H$_2$SO$_4$. The standard curve was created by using the SoftMax Pro software (Molecular Devices) to generate a four parameter logistic curve-fit and used to calculate the concentrations of IgE in all tested samples. Student t tests were used to compare data by using the Prism software. As shown in FIGS. 17a and 17b, hu8D6 at 10 mg/ml in the initiation of cultures reduced culture IgE levels by 88.1%, 93.4%, and 88.6%, while Omalizumab reduced IgE levels by 21.3%, 26.4, and 30% at 7-, 11- and 14-day incubation, respectively. The results suggest that hu8D6 capable of binding membrane-bound and CD23-bound IgE on B cells is superior to Omalizumab, which doesn't bind IgE already bound by CD23, in inhibiting the de novo IgE synthesis.

---

The invention claimed is:

1. A humanized antibody, which binds to free IgE, membrane-bound IgE on B lymphocytes, or IgE bound by CD23, but not to IgE bound by FcεRI, wherein the humanized antibody comprises a heavy chain variable region ($V_H$) and a light chain variable region ($V_L$), wherein the $V_H$ comprises an amino acid sequence that is identical to SEQ ID NO: 2, and the hypervariable regions of $V_H$ are positions 26-35 (CDR-H1; SEQ ID NO: 5), 50-65 (CDR-H2; SEQ ID NO: 6) and 93-104 (CDR-H3; SEQ ID NO: 7); and the $V_L$ comprises an amino acid sequence that is identical to SEQ ID NO: 4, and the hypervariable regions of $V_L$ are positions 27-34 (CDR-L1; SEQ ID NO: 8), 50-56 (CDR-L2; SEQ ID NO: 9), and 89-97 (CDR-L3; SEQ ID NO: 10).

2. The humanized antibody of claim 1, which crosslinks IgE-bound CD23 on B lymphocytes.

3. The humanized antibody of claim 1, which decreases the total IgE production by B lymphocytes.

4. The humanized antibody of claim 1, which decreases the antigen-specific IgE production by antigen-activated B lymphocytes.

5. The humanized antibody of claim 1, which decreases IgE production in patients treated with the humanized antibody.

6. The humanized antibody of claim 1, wherein the antibody is an antigen-binding fragment.

7. The humanized antibody of claim 6, wherein the antigen-binding fragment is Fab, F(ab')2, or single-chain Fv.

8. The humanized antibody of claim 1, wherein the $V_H$ and $V_L$ of the humanized antibody are derived from human B lymphocytes.

9. A pharmaceutical composition, comprising a therapeutically-effective amount of the humanized antibody of claim 1 and a pharmaceutically acceptable carrier.

10. A method for treating an IgE-mediated disease, comprising administering to a patient in need thereof an effective amount of the humanized antibody of claim 1.

11. The method of claim 10, wherein the IgE-mediated disease is allergic asthma, allergic rhinitis, atopic dermatitis, food allergy, chronic spontaneous (idiopathic) urticaria, chronic rhinosinusitis, systemic mastocytosis, cutaneous mastocytosis, allergic bronchopulmonary aspergillosis, recurrent idiopathic angioedema, or eosinophil-associated gastrointestinal disorder.

12. The method of claim 10, wherein the humanized antibody induces the degranulation of mast cells and basophils.

13. The method of claim 10, wherein the humanized antibody and IgE form an immune complex in the patient, and the immune complex is capable of binding to CD23 and crosslinking CD23; but incapable of binding to FcεRI and inducing the degranulation of mast cells and basophils.

* * * * *